(12) United States Patent
Rodriguez et al.

(10) Patent No.: US 10,790,456 B2
(45) Date of Patent: Sep. 29, 2020

(54) MATERIALS FOR ELECTRONIC DEVICES

(71) Applicant: Merck Patent GmbH, Darmstadt (DE)

(72) Inventors: Lara-Isabel Rodriguez, Darmstadt (DE); Linge Rouven, Darmstadt (DE); Sebastian Meyer, Aschaffenburg (DE); Holger Heil, Frankfurt am Main (DE); Beate Burkhart, Darmstadt (DE)

(73) Assignee: Merck Patent GmbH (DE)

( * ) Notice: Subject to any disclaimer, the term of this patent is extended or adjusted under 35 U.S.C. 154(b) by 412 days.

(21) Appl. No.: 15/751,969

(22) PCT Filed: Jul. 13, 2016

(86) PCT No.: PCT/EP2016/001205
§ 371 (c)(1),
(2) Date: Feb. 12, 2018

(87) PCT Pub. No.: WO2017/025165
PCT Pub. Date: Feb. 16, 2017

(65) Prior Publication Data
US 2018/0240985 A1    Aug. 23, 2018

(30) Foreign Application Priority Data

Aug. 12, 2015 (EP) .................................... 15180777

(51) Int. Cl.
C07D 493/04 (2006.01)
H01L 51/00 (2006.01)
C09K 11/06 (2006.01)
C09B 23/14 (2006.01)
C09B 1/00 (2006.01)
C09B 57/00 (2006.01)
C07D 497/04 (2006.01)
H01L 51/50 (2006.01)

(52) U.S. Cl.
CPC ........ *H01L 51/0073* (2013.01); *C07D 493/04* (2013.01); *C07D 497/04* (2013.01); *C09B 1/00* (2013.01); *C09B 23/148* (2013.01); *C09B 57/00* (2013.01); *C09B 57/001* (2013.01); *C09B 57/008* (2013.01); *C09K 11/06* (2013.01); *H01L 51/0052* (2013.01); *H01L 51/0058* (2013.01); *C09K 2211/1007* (2013.01); *C09K 2211/1011* (2013.01); *C09K 2211/1014* (2013.01); *C09K 2211/1018* (2013.01); *C09K 2211/1059* (2013.01); *C09K 2211/1088* (2013.01); *H01L 51/5012* (2013.01); *H01L 51/5016* (2013.01); *H01L 51/5056* (2013.01); *Y02E 10/549* (2013.01)

(58) Field of Classification Search
CPC ...................... C07D 497/04; C09K 2211/1088
See application file for complete search history.

(56) References Cited

U.S. PATENT DOCUMENTS

2008/0220285 A1   9/2008   Vestweber et al.
2009/0184313 A1   7/2009   Buesing et al.
2013/0053558 A1   2/2013   Pflumm et al.

FOREIGN PATENT DOCUMENTS

| DE | 102006025846 A1 |   | 12/2007 |
|----|----|----|----|
| DE | 102009052428 A1 |   | 5/2011 |
| JP | 2007119392 A | * | 5/2007 |
| JP | 2010045281 A |   | 2/2010 |
| WO | 2006122630 A1 |   | 11/2006 |

\* cited by examiner

*Primary Examiner* — Jennifer A Chriss
*Assistant Examiner* — Sean M DeGuire
(74) *Attorney, Agent, or Firm* — Faegre Drinker Biddle & Reath LLP

(57) ABSTRACT

The present application relates to compounds of a formula (I), to the use thereof in organic electroluminescent devices, and to processes for preparing these compounds.

17 Claims, No Drawings

MATERIALS FOR ELECTRONIC DEVICES

RELATED APPLICATIONS

This application is a national stage entry, filed pursuant to 35 U.S.C. § 371, of PCT/EP2016/001205, filed Jul. 13, 2016, which claims the benefit of European Patent Application No. 15180777.3, filed Aug. 12, 2015, which is incorporated herein by reference in its entirety.

The present application relates to heteroaromatic compounds of a formula (I) defined in detail below, which are suitable for use as functional materials in electronic devices.

The term "electronic device" is understood according to the present invention to mean electronic devices in general that contain organic materials. This is preferably understood to mean organic electroluminescent devices (OLEDs).

With regard to the performance data of the electronic devices, further improvements are required in principle, especially with regard to broad commercial use, for example in displays or as light sources. Of particular significance in this connection are the lifetime, the efficiency and the operating voltage of the electronic devices, and the colour values achieved. Especially in the case of blue-fluorescing OLEDs, there is potential for improvement with regard to efficiency, the lifetime of the devices and the colour values of the light emitted.

An important starting point for achieving the improvements mentioned is the choice of compound which is used as matrix in the emitting layer of the electronic device, preferably in combination with a fluorescent emitter compound. It is of particular interest here that the compounds permit triplet-triplet annihilation (TTA), since the efficiency of the device is enhanced as a result.

A matrix in the emitting layer is understood in the context of the present application to mean those compounds that are present in the emitting layer of the device but are not emitter compounds, meaning that they are involved only insignificantly, if at all, in the light emission of the emitting layer. Emitter compounds are correspondingly understood to mean compounds in the emitting layer which emit light on operation of the device. The term "fluorescent emitters", according to the present application, encompasses compounds where the light is emitted from a singlet state.

In the context of the present invention, it has been found that compounds of the formula (I) defined below are of excellent suitability as functional materials for electronic devices, and especially bring about a high quantum efficiency, deep blue colour coordinates and a long lifetime of the devices. Furthermore, the compounds have high thermal stability. Furthermore again, the compounds have a low triplet level, and are therefore especially suitable for use as matrix compound in the emitting layer of OLEDs in which triplet-triplet annihilation takes place.

The application therefore provides a compound of formula (I)

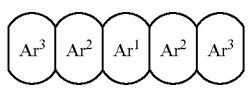

Formula (I)

where the variables that occur are:

is a benzene ring which may be substituted in each case by $R^1$ radicals;

is the same or different at each instance and is selected from units of the formula ($Ar^2$-1) or ($Ar^2$-2)

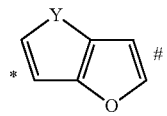

Formula ($Ar^2$-1)

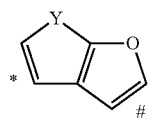

Formula ($Ar^2$-2)

where the bond marked with * is that bond via which the unit is fused to the $Ar^1$ group, and the bond marked with # is that bond via which the unit is fused to the $Ar^3$ group;
Y is the same or different at each instance and is $C(R^2)_2$ or $Si(R^2)_2$;

is the same or different at each instance and is selected from aromatic ring systems having 6 to 30 aromatic ring atoms or heteroaromatic ring systems having 5 to 30 aromatic ring atoms, each of which may be substituted by $R^3$ radicals;
$R^1$, $R^2$, $R^3$ are the same or different at each instance and are selected from H, D, F, $C(=O)R^4$, CN, $Si(R^4)_3$, $N(R^4)_2$, $P(=O)(R^4)_2$, $OR^4$, $S(=O)R^4$, $S(=O)_2R^4$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more $R^1$, $R^2$ and/or $R^3$ radicals may be joined to one another and may form a ring; where the alkyl, alkoxy, alkenyl and alkynyl groups mentioned and the aromatic ring systems and heteroaromatic ring systems mentioned may each be substituted by one or more $R^4$ radicals; and where one or more $CH_2$ groups in the alkyl, alkoxy, alkenyl and alkynyl groups mentioned may be replaced by —$R^4C=CR^4$—, —C≡C—, $Si(R^4)_2$, C=O, C=$NR^4$, —C(=O)O—, —C(=O)$NR^4$—, $NR^4$, $P(=O)(R^4)$, —O—, —S—, SO or $SO_2$;
$R^4$ is the same or different at each instance and is selected from H, D, F, $C(=O)R^5$, CN, $Si(R^5)_3$, $N(R^5)_2$, $P(=O)(R^5)_2$, $OR^5$, $S(=O)R^5$, $S(=O)_2R^5$, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; where two or more R⁴ radicals may be joined to one another and may form a ring; where the alkyl, alkoxy, alkenyl and alkynyl groups mentioned and the aromatic ring systems and heteroaromatic ring systems mentioned may each be substituted by one or more R⁵ radicals; and where one or more CH₂ groups in the alkyl, alkoxy, alkenyl and alkynyl groups mentioned may be replaced by —R⁵C=CR⁵—, —C≡C—, Si(R⁵)₂, C=O, C=NR⁵, —C(=O)O—, —C(=O)NR⁵—, NR⁵, P(=O)(R⁵), —O—, —S—, SO or SO₂;

R⁵ is the same or different at each instance and is selected from H, D, F, CN, alkyl groups having 1 to 20 carbon atoms, aromatic ring systems having 6 to 40 aromatic ring atoms and heteroaromatic ring systems having 5 to 40 aromatic ring atoms; where two or more R⁵ radicals may be joined to one another and may form a ring; and where the alkyl groups, aromatic ring systems and heteroaromatic ring systems mentioned may be substituted by F or CN.

For reasons of clarity, the

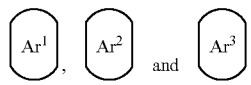

groups are referred to hereinafter without their graphic symbol, i.e. merely as "Ar¹", "Ar²" and "Ar³" respectively.

Two adjacent Ar¹, Ar² or Ar³ units are always fused to one another via a common bond, in the way in which two benzene rings are fused via a common bond to form a naphthyl group.

Preferably, the bonds via which the Ar¹, Ar² and Ar³ groups are fused to one another are bonds between two carbon atoms, preferably between two sp²-hybridized carbon atoms. Formula (I) thus corresponds to the following preferred formula (I-C):

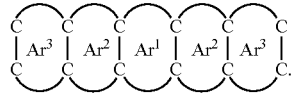

Formula (I-C)

An aryl group in the context of this invention contains 6 to 40 aromatic ring atoms of which none is a heteroatom. An aryl group in the context of this invention is understood to mean either a simple aromatic cycle, i.e. benzene, or a fused aromatic polycycle, for example naphthalene, phenanthrene or anthracene. A fused aromatic polycycle in the context of the present application consists of two or more simple aromatic cycles fused to one another. Fusion between cycles is understood here to mean that the cycles share at least one edge with one another.

A heteroaryl group in the context of this invention contains 5 to 40 aromatic ring atoms of which at least one is a heteroatom. The heteroatoms of the heteroaryl group are preferably selected from N, O and S. A heteroaryl group in the context of this invention is understood to mean either a simple heteroaromatic cycle, for example pyridine, pyrimidine or thiophene, or a fused heteroaromatic polycycle, for example quinoline or carbazole. A fused heteroaromatic polycycle in the context of the present application consists of two or more simple heteroaromatic cycles fused to one another. Fusion between cycles is understood here to mean that the cycles share at least one edge with one another.

An aryl or heteroaryl group, each of which may be substituted by the abovementioned radicals and which may be joined to the aromatic or heteroaromatic system via any desired positions, is especially understood to mean groups derived from benzene, naphthalene, anthracene, phenanthrene, pyrene, dihydropyrene, chrysene, perylene, triphenylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the context of this invention contains 6 to 40 carbon atoms in the ring system and does not include any heteroatoms as aromatic ring atoms. An aromatic ring system in the context of this invention therefore does not contain any heteroaryl groups. An aromatic ring system in the context of this invention shall be understood to mean a system which does not necessarily contain only aryl groups but in which it is also possible for a plurality of aryl groups to be bonded by a single bond or by a nonaromatic unit, for example one or more optionally substituted C, Si, N, O or S atoms. In this case, the nonaromatic unit comprises preferably less than 10% of the atoms other than H, based on the total number of atoms other than H in the system. For example, systems such as 9,9'-spirobifluorene, 9,9'-diarylfluorene, triarylamine, diaryl ethers and stilbene are also to be regarded as aromatic ring systems in the context of this invention, and likewise systems in which two or more aryl groups are joined, for example, by a linear or cyclic alkyl, alkenyl or alkynyl group or by a silyl group. In addition, systems in which two or more aryl groups are joined to one another via single bonds are also to be regarded as aromatic ring systems in the context of this invention, for example systems such as biphenyl and terphenyl.

A heteroaromatic ring system in the context of this invention contains 5 to 40 aromatic ring atoms, at least one of which is a heteroatom. The heteroatoms of the heteroaromatic ring system are preferably selected from N, O and/or S. A heteroaromatic ring system corresponds to the abovementioned definition of an aromatic ring system, but has at least one heteroatom as one of the aromatic ring atoms. In this way, it differs from an aromatic ring system in the sense of the definition of the present application, which, according to this definition, cannot contain any heteroatom as aromatic ring atom.

An aromatic ring system having 6 to 40 aromatic ring atoms or a heteroaromatic ring system having 5 to 40 aromatic ring atoms is especially understood to mean groups derived from the groups mentioned above under aryl groups and heteroaryl groups, and from biphenyl, terphenyl, quaterphenyl, fluorene, spirobifluorene, dihydrophenanthrene, dihydropyrene, tetrahydropyrene, indenofluorene, truxene, isotruxene, spirotruxene, spiroisotruxene, indenocarbazole, or from combinations of these groups.

In the context of the present invention, a straight-chain alkyl group having 1 to 20 carbon atoms and a branched or cyclic alkyl group having 3 to 20 carbon atoms and an alkenyl or alkynyl group having 2 to 40 carbon atoms in which individual hydrogen atoms or $CH_2$ groups may also be substituted by the groups mentioned above in the definition of the radicals are preferably understood to mean the methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl radicals.

An alkoxy or thioalkyl group having 1 to 20 carbon atoms in which individual hydrogen atoms or $CH_2$ groups may also be replaced by the groups mentioned above in the definition of the radicals is preferably understood to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The wording that two or more radicals together may form a ring, in the context of the present application, shall be understood to mean, inter alia, that the two radicals are joined to one another by a chemical bond. In addition, however, the abovementioned wording shall also be understood to mean that, if one of the two radicals is hydrogen, the second radical binds to the position to which the hydrogen atom was bonded, forming a ring.

Preferably, the compounds of the formula (I) are symmetric with respect to a mirror plane through the middle and at right angles to the longitudinal axis of the elongated molecule, especially through the middle of the $Ar^1$ group. This means that the right-hand side and the left-hand side of the molecule, each viewed from the middle, i.e. from the $Ar^1$ group, are the same. More preferably, this applies not just to the base skeleton but also to the entire compound, i.e. with inclusion of the substituents. However, the general formula also encompasses asymmetric compounds, especially those that are symmetric with respect to the base skeleton of the formula (I) but are asymmetric as a whole because of their substitution.

Preferably, $Ar^1$ corresponds to one of the formulae ($Ar^1$-1) and ($Ar^1$-2) shown below

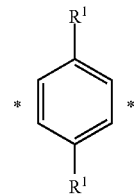

Formula ($Ar^1$-1)

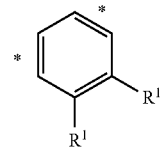

Formula ($Ar^1$-2)

where the bonds marked with * are those bonds via which the $Ar^1$ group in question is fused to the two adjacent $Ar^2$ groups.

Among the formulae ($Ar^1$-1) and ($Ar^1$-2), particular preference is given to the formula ($Ar^1$-1).

Preferably, in formula ($Ar^1$-1) and ($Ar^1$-2), the $R^1$ groups are H.

Preferably, $Ar^2$ is selected from groups of the formula ($Ar^2$-1).

Preferably, the Y group is $C(R^2)_2$. Particular preference is given to the selection of $Ar^2$ corresponding to formula ($Ar^2$-1), and the simultaneous selection of Y as $C(R^2)_2$.

Preferably, $Ar^3$ is the same or different at each instance and is selected from benzene, pyridine, pyrimidine, pyrazine, pyridazine, pyrrole, furan, thiophene, benzofuran, benzothiophene, dibenzofuran, dibenzothiophene, fluorene, spirobifluorene, indenofluorene, naphthalene and anthracene, each of which may be substituted by $R^3$ radicals. Among these, particular preference is given to benzene, naphthalene, fluorene and spirobifluorene, each of which may be substituted by $R^3$ radicals.

Preferred $Ar^3$ groups are selected from the following groups:

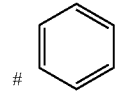

Formula ($Ar^3$-1)

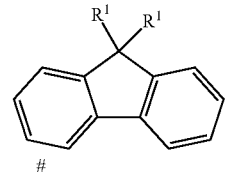

Formula ($Ar^3$-2)

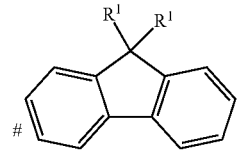

Formula ($Ar^3$-3)

-continued

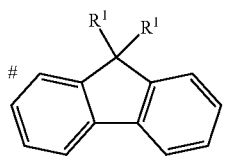
Formula (Ar³-4)
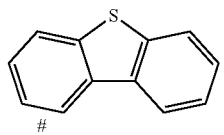

Formula (Ar³-13)
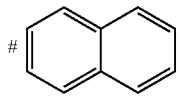

Formula (Ar³-5)
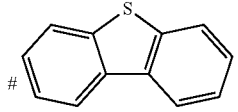

Formula (Ar³-14)
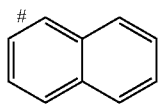

Formula (Ar³-6)
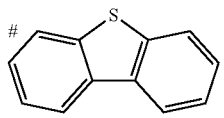

Formula (Ar³-15)
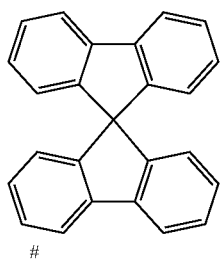

Formula (Ar³-7)
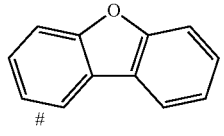

Formula (Ar³-16)
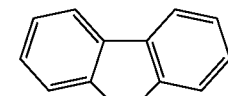

Formula (Ar³-8)
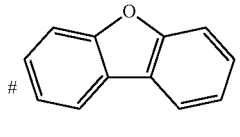

Formula (Ar³-17)
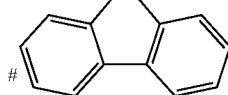

Formula (Ar³-9)
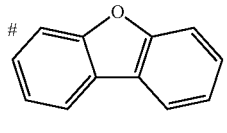

Formula (Ar³-18)

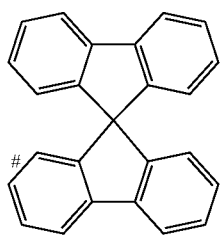

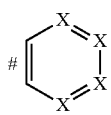
Formula (Ar³-10)

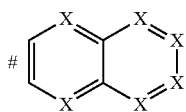
Formula (Ar³-11)

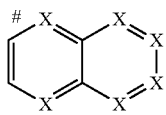
Formula (Ar³-12)

where the bond marked with # is that bond via which the Ar¹ group in question is fused to the adjacent Ar² group, where the groups may be substituted by R³ radicals at the positions shown as unsubstituted, and where X is the same or different at each instance and is N or CR³.

Preferably, not more than three X groups in a six-membered ring are N. Further preferably, not more than two adjacent X groups are N.

Preferred R¹ groups are the same or different at each instance and are selected from H, F, CN, alkyl groups having 1 to 20 carbon atoms, aromatic ring systems having 6 to 30 aromatic ring atoms and heteroaromatic ring systems having 5 to 30 aromatic ring atoms; where two or more R¹ radicals may be joined to one another and may form a ring; and where the alkyl groups, aromatic ring systems and heteroaromatic ring systems mentioned may be substituted by R⁴ and may preferably be substituted by F or CN.

Preferred R² groups are the same or different at each instance and are selected from straight-chain alkyl groups having 1 to 20 carbon atoms, branched or cyclic alkyl groups having 3 to 20 carbon atoms, aromatic ring systems having 6 to 18 aromatic ring atoms and heteroaromatic ring systems having 5 to 18 aromatic ring atoms, where the groups mentioned may be substituted by R⁴ radicals. Particularly preferred R² groups are the same or different at each instance and are selected from methyl, ethyl, propyl, butyl, pentyl, hexyl, heptyl, octyl, nonyl, decyl and phenyl, each of which may be substituted by R⁴ radicals and are preferably unsubstituted.

Preferred R³ groups are the same or different at each instance and are selected from H, F, CN, alkyl groups having 1 to 20 carbon atoms, aromatic ring systems having 6 to 30 aromatic ring atoms and heteroaromatic ring systems having 5 to 30 aromatic ring atoms; where two or more $R^3$ radicals may be joined to one another and may form a ring; and where the alkyl groups, aromatic ring systems and heteroaromatic ring systems mentioned may be substituted by $R^4$ and may preferably be substituted by F or CN.

Preferred embodiments of the formula (I) correspond to the following formula:

Formula (I-1)

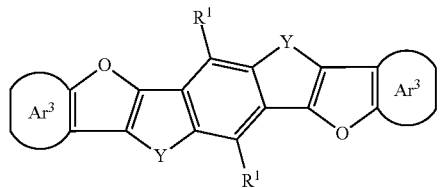

where the symbols that occur are as defined above, and where the Y group is preferably $C(R^2)_2$, and where the $Ar^3$ groups preferably correspond to the above-specified groups of the formulae $(Ar^3-1)$ to $(Ar^3-9)$.

The $Ar^3$ group in the preferred formula (I-1), as elucidated above for formula (I), is fused to the furan unit via a common bond.

Preferably, the above-specified preferred embodiments of the variable groups apply to formula (I-1).

A particularly preferred embodiment of the compounds according to the application is an embodiment for which the following combined conditions apply:
the base skeleton corresponds to the formula (I-1);
Y is $C(R^2)_2$;
the $Ar^3$ groups correspond to a formula selected from the formulae $(Ar^3-1)$ to $(Ar^3-9)$, preferably to the formula $(Ar^3-1)$.

The compound of the formula (I) is preferably characterized in that the value of its triplet level is greater than the value of its singlet level divided by 2. The values of singlet energy level and triplet energy level are determined by quantum-mechanical calculation, as specified in the working examples of WO 2015/036080, section A).

The following compounds are examples of compounds of formula (I):

(1)

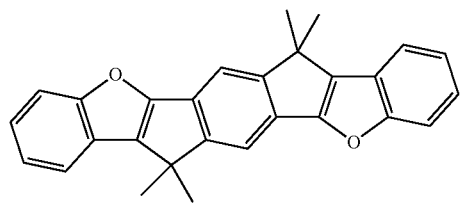

(2)

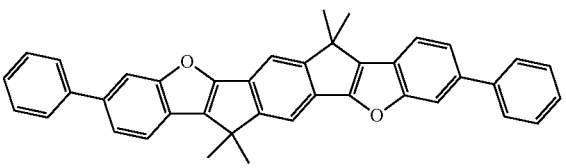

(3)

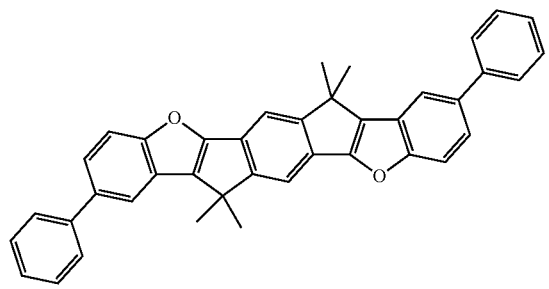

(4)

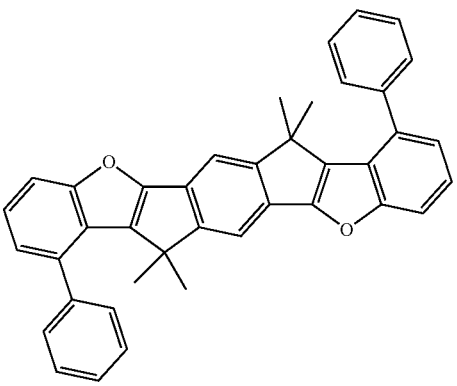

(5)

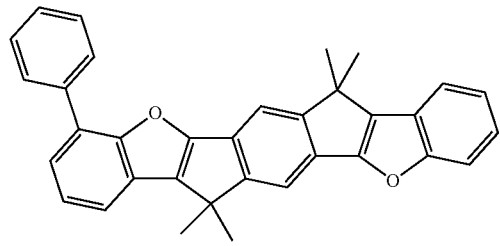

(6)

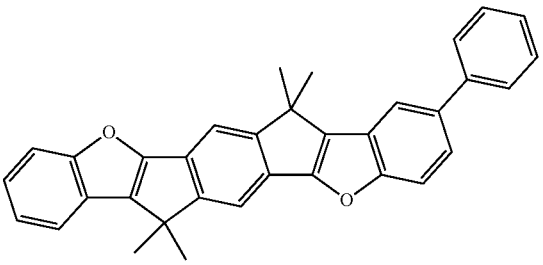

-continued
(7)
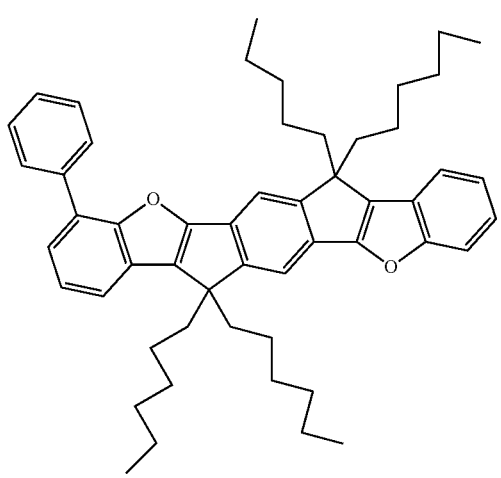
(8)
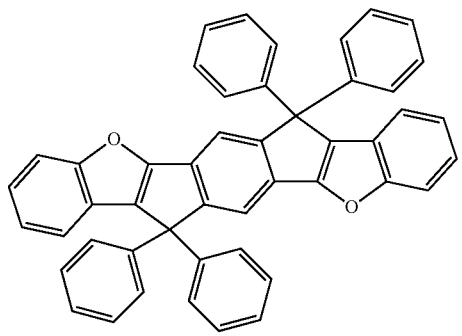
(9)
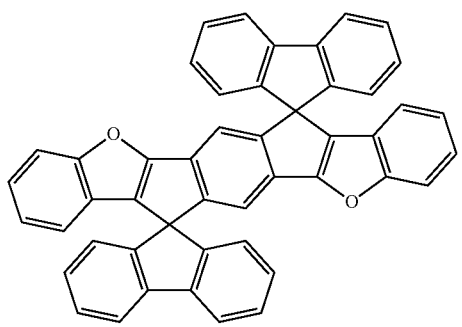
(10)
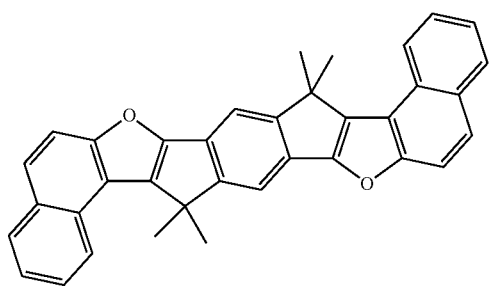
(11)
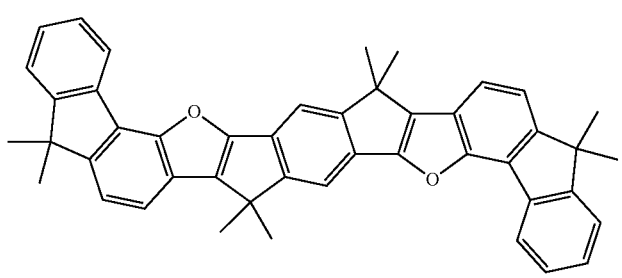
(12)
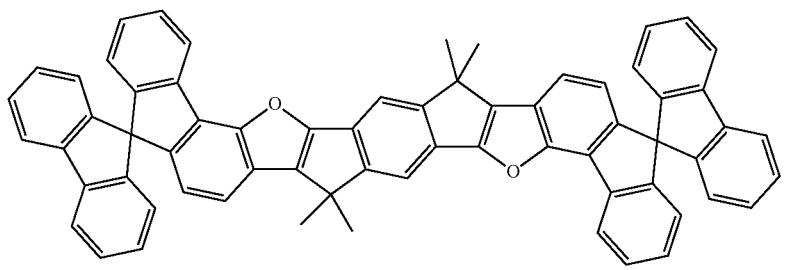

-continued
(13)
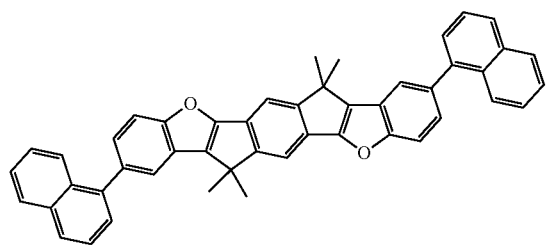
(14)
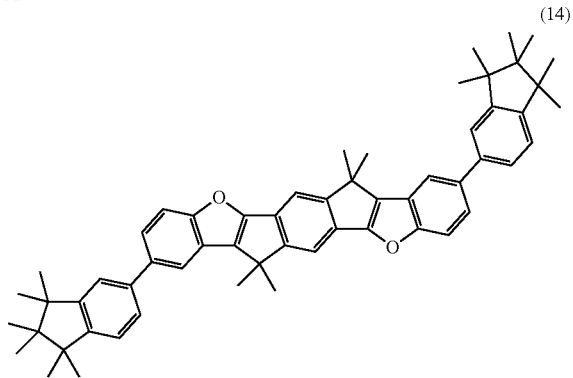
(15)
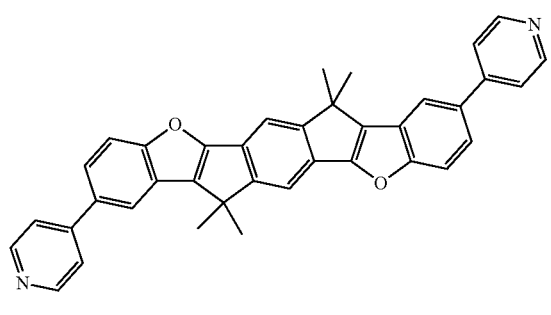
(16)
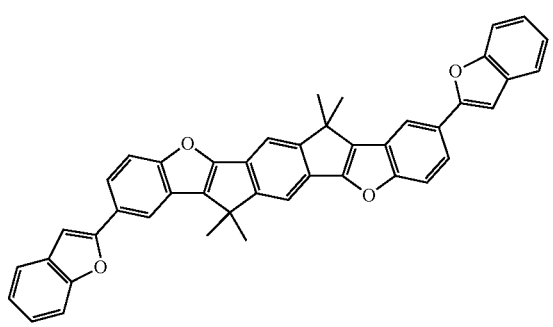
(17)
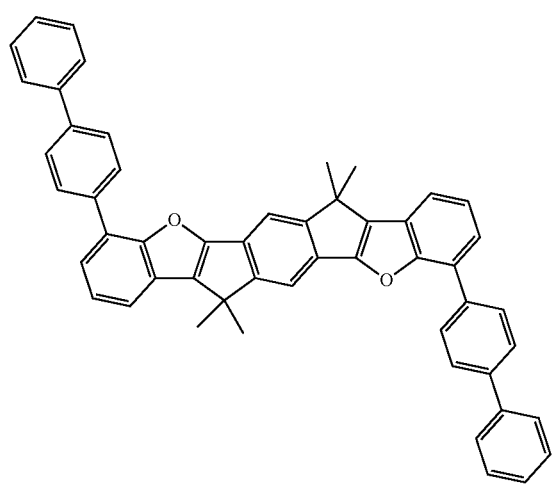
(18)
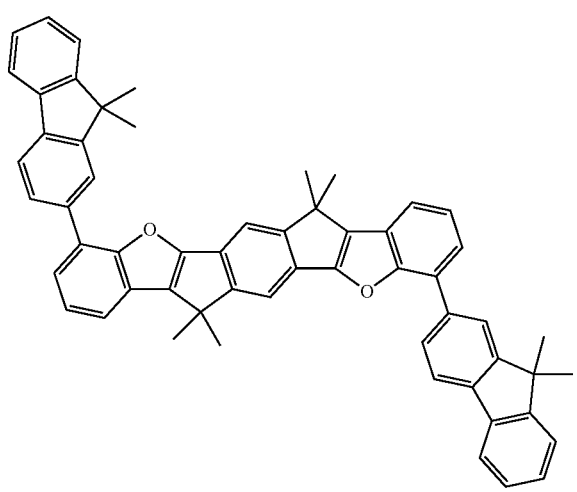

-continued
(19)
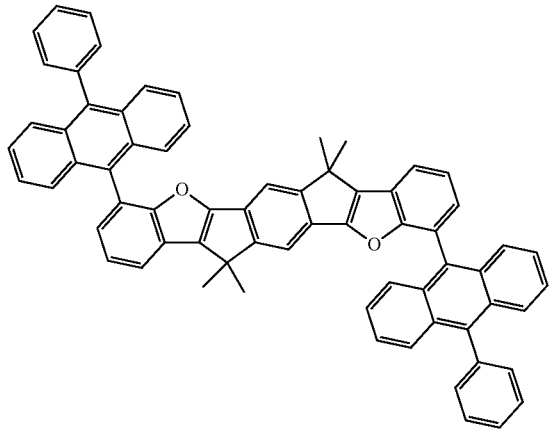
(20)
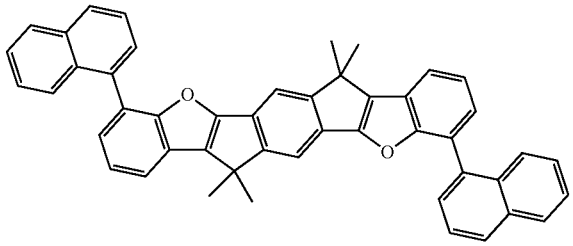
(21)
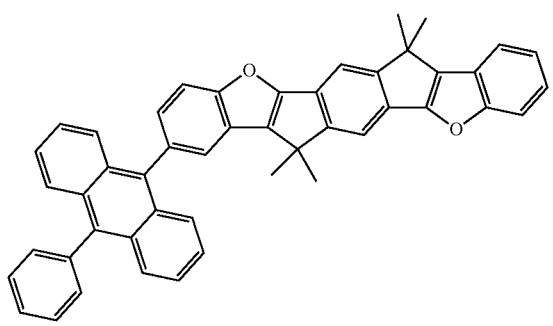
(22)
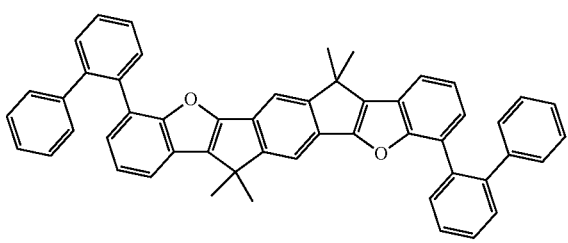
(23)
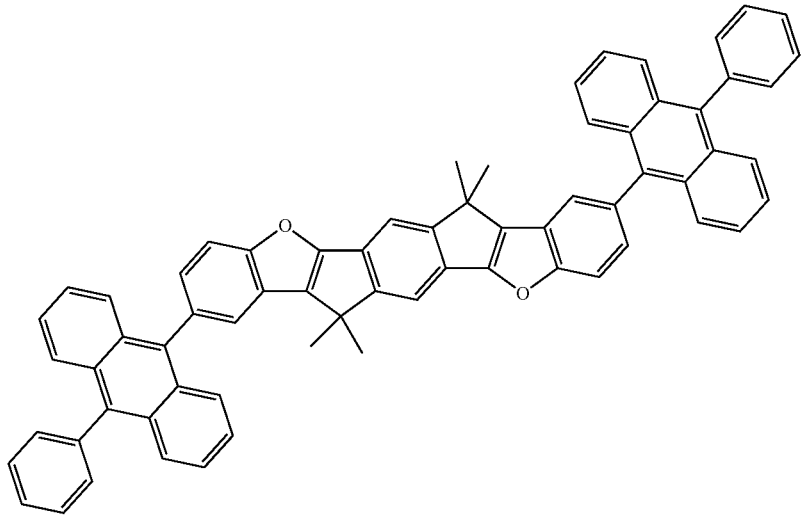
(24)
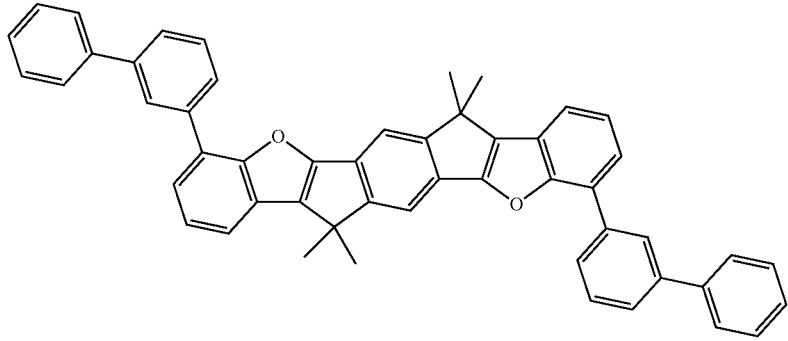

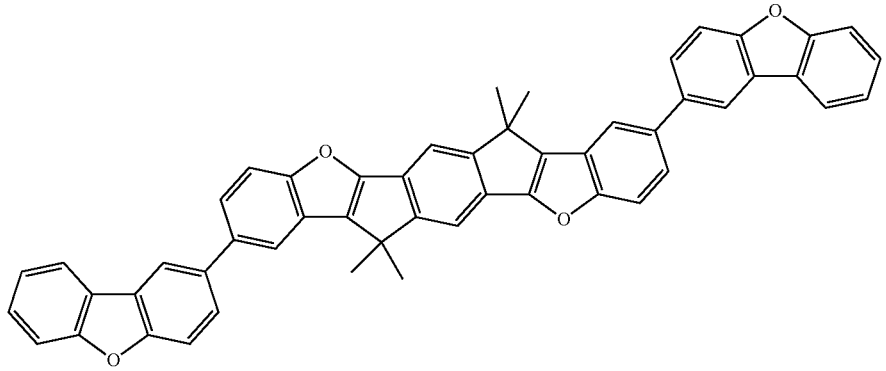
(25)

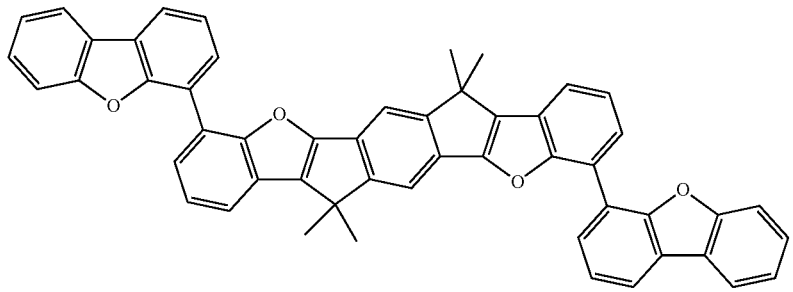
(26)

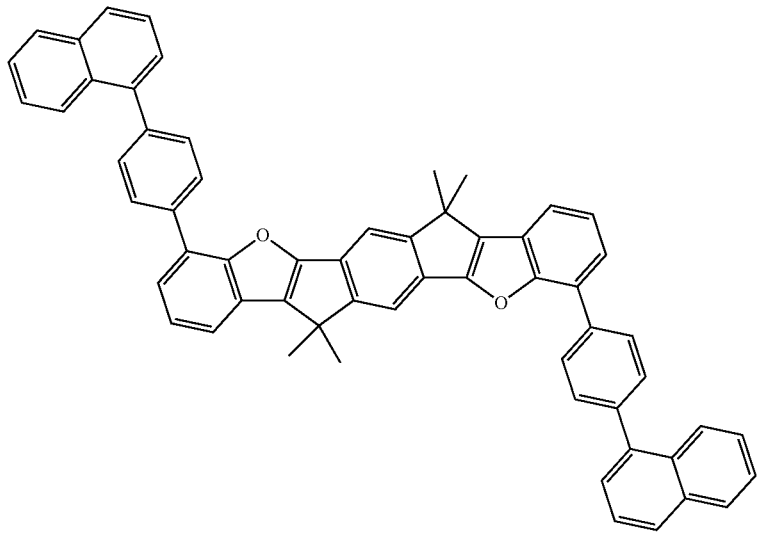
(27)

The compounds according to the present application can be prepared, for example, as follows (cf. general scheme of the working examples under A-1)):

For this purpose, in a first step, two furan-containing groups I which may also include the Ar³ unit are joined to the central Ar¹ unit via an organometallic coupling reaction. The central unit here is difunctional, and so two equivalents of the furan-containing compound react with one equivalent of the central Ar¹ unit.

In a second step, the ring-closure reaction which occurs twice and which forms the Ar² units is prepared. This occurs by reduction of two ester groups on the Ar¹ unit to give a tertiary alcohol group, preferably by means of an alkylmagnesium compound.

In a third step, the ring-closure reaction that occurs twice is executed, by adding acid. This affords the base skeleton of the compound of the formula (I). The latter can, as shown in the general scheme under A-2, be modified further preferably by bromination and subsequent introduction of aromatic groups by organometallic coupling reaction.

The synthesis of compounds of the formula (I) containing silyl bridges (Y=Si(R²)₂) can be effected, for example, by the methods described in Q.-W. Zhang et al., Synlett 2015, 26, 1145-1152.

For the synthesis of unsymmetrically substituted compounds (cf. scheme below), it is possible to proceed from a terephthalic acid derivative substituted by two different halogen groups, which is joined sequentially first to a benzofuran unit and then to a second benzofuran unit. The further steps (reduction to the tertiary alcohol and ring closure under the action of acid) correspond to those shown in the scheme in A-1) for the symmetric derivatives. In this way, it is possible to obtain compounds which bear different substituents on the two terminal benzofuran groups.

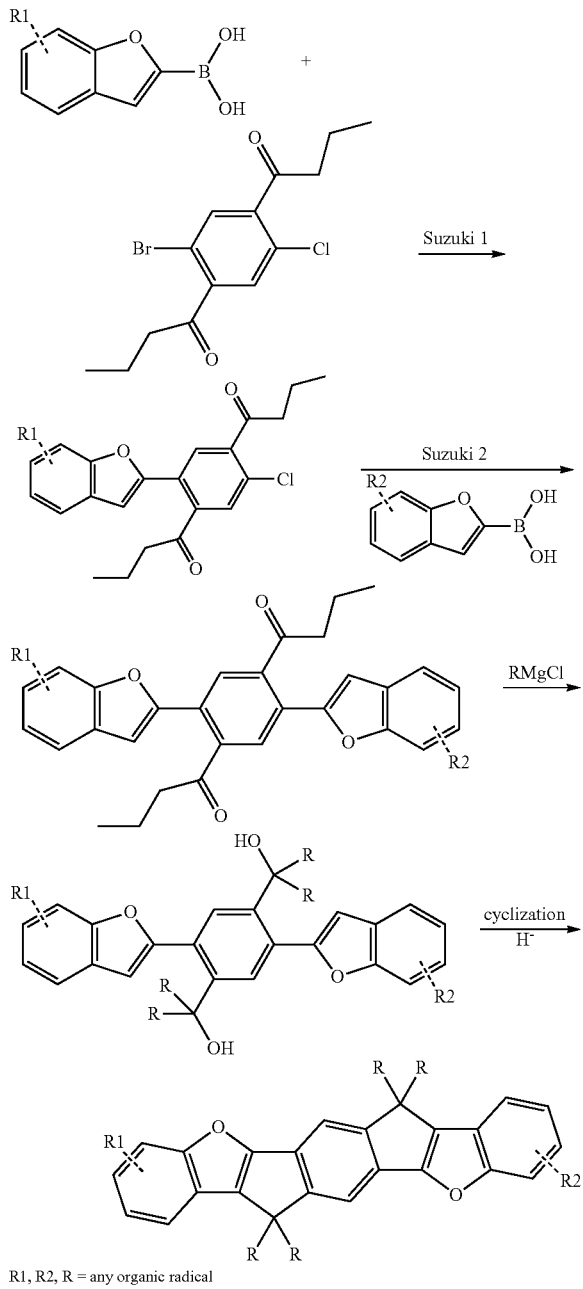

R1, R2, R = any organic radical

The present application therefore also provides a process for preparing compounds of the formula (I), characterized in that the compound is formed by the following steps conducted in the present sequence:
i) an organometallic coupling reaction between two compounds each containing a furan group and a compound containing the $Ar^1$ unit,
ii) the subsequent reduction of an ester group bonded to the $Ar^1$ unit and present in the compound to a tertiary alcohol group bonded to the same $Ar^1$ unit, and finally
iii) a ring-closure reaction of this tertiary alcohol group to form an alkylene bridge between the $Ar^1$ unit and the furan ring.

The above-described compounds of the invention, especially compounds substituted by reactive leaving groups, such as bromine, iodine, chlorine, boronic acid or boronic ester, may find use as monomers for production of corresponding oligomers, dendrimers or polymers. Suitable reactive leaving groups are, for example, bromine, iodine, chlorine, boronic acids, boronic esters, amines, alkenyl or alkynyl groups having a terminal C—C double bond or C—C triple bond, oxiranes, oxetanes, groups which enter into a cycloaddition, for example a 1,3-dipolar cycloaddition, for example dienes or azides, carboxylic acid derivatives, alcohols and silanes.

The invention therefore further provides oligomers, polymers or dendrimers containing one or more compounds of formula (I), wherein the bond(s) to the polymer, oligomer or dendrimer may be localized at any desired positions substituted by $R^1$, $R^2$ or $R^3$ in formula (I). According to the linkage of the compound of formula (I), the compound is part of a side chain of the oligomer or polymer or part of the main chain. An oligomer in the context of this invention is understood to mean a compound formed from at least three monomer units. A polymer in the context of the invention is understood to mean a compound formed from at least ten monomer units. The polymers, oligomers or dendrimers of the invention may be conjugated, partly conjugated or nonconjugated. The oligomers or polymers of the invention may be linear, branched or dendritic. In the structures having linear linkage, the units of formula (I) may be joined directly to one another, or they may be joined to one another via a bivalent group, for example via a substituted or unsubstituted alkylene group, via a heteroatom or via a bivalent aromatic or heteroaromatic group. In branched and dendritic structures, it is possible, for example, for three or more units of formula (I) to be joined via a trivalent or higher-valency group, for example via a trivalent or higher-valency aromatic or heteroaromatic group, to give a branched or dendritic oligomer or polymer.

The corresponding polymers containing units of the formula (I) can be used, for example, as triplet control polymer for triplet-triplet annihilation. The groups of the formula (I) may replace anthracene groups in an equivalent manner.

For the repeat units of formula (I) in oligomers, dendrimers and polymers, the same preferences apply as described above for compounds of formula (I).

For preparation of the oligomers or polymers, the monomers of the invention are homopolymerized or copolymerized with further monomers. Suitable and preferred comonomers are chosen from fluorenes (for example according to EP 842208 or WO 00/22026), spirobifluorenes (for example according to EP 707020, EP 894107 or WO 06/061181), paraphenylenes (for example according to WO 1992/18552), carbazoles (for example according to WO 04/070772 or WO 2004/113468), thiophenes (for example according to EP 1028136), dihydrophenanthrenes (for example according to WO 2005/014689 or WO 2007/006383), cis- and trans-indenofluorenes (for example according to WO 2004/041901 or WO 2004/113412), ketones (for example according to WO 2005/040302), phenanthrenes (for example according to WO 2005/104264 or WO 2007/017066) or else a plurality of these units. The polymers, oligomers and dendrimers typically contain still further units, for example emitting (fluorescent or phosphorescent) units, for example vinyltriarylamines (for example according to WO 2007/068325) or phosphorescent metal complexes (for example according to WO 2006/003000), and/or charge transport units, especially those based on triarylamines.

The polymers and oligomers of the invention are generally prepared by polymerization of one or more monomer types, of which at least one monomer leads to repeat units of the formula (I) in the polymer. Suitable polymerization reactions are known to those skilled in the art and are described in the literature. Particularly suitable and preferred polymerization reactions which lead to C—C and C—N bonds are as follows:
(A) SUZUKI polymerization;
(B) YAMAMOTO polymerization;
(C) STILLE polymerization; and
(D) HARTWIG-BUCHWALD polymerization.

How the polymerization can be conducted by these methods and how the polymers can then be separated from the reaction medium and purified is known to those skilled in the art and is described in detail in the literature, for example in WO 2003/048225, WO 2004/037887 and WO 2004/037887.

For the processing of the compounds of the invention from the liquid phase, for example by spin-coating or by printing methods, formulations of the compounds of the invention are required. These formulations may, for example, be solutions, dispersions or emulsions. For this purpose, it may be preferable to use mixtures of two or more solvents. Suitable and preferred solvents are, for example, toluene, anisole, o-, m- or p-xylene, methyl benzoate, mesitylene, tetralin, veratrole, THF, methyl-THF, THP, chlorobenzene, dioxane, phenoxytoluene, especially 3-phenoxytoluene, (−)-fenchone, 1,2,3,5-tetramethylbenzene, 1,2,4,5-tetramethylbenzene, 1-methylnaphthalene, 2-methylbenzothiazole, 2-phenoxyethanol, 2-pyrrolidinone, 3-methylanisole, 4-methylanisole, 3,4-dimethylanisole, 3,5-dimethylanisole, acetophenone, α-terpineol, benzothiazole, butyl benzoate, cumene, cyclohexanol, cyclohexanone, cyclohexylbenzene, decalin, dodecylbenzene, ethyl benzoate, indane, methyl benzoate, NMP, p-cymene, phenetole, 1,4-diisopropylbenzene, dibenzyl ether, diethylene glycol butyl methyl ether, triethylene glycol butyl methyl ether, diethylene glycol dibutyl ether, triethylene glycol dimethyl ether, diethylene glycol monobutyl ether, tripropylene glycol dimethyl ether, tetraethylene glycol dimethyl ether, 2-isopropylnaphthalene, pentylbenzene, hexylbenzene, heptylbenzene, octylbenzene, 1,1-bis(3,4-dimethylphenyl)ethane or mixtures of these solvents.

The invention therefore further provides a formulation, especially a solution, dispersion or emulsion, comprising at least one compound of formula (I) or at least one polymer, oligomer or dendrimer containing at least one unit of formula (I) and at least one solvent, preferably an organic solvent. The way in which such solutions can be prepared is known to those skilled in the art and is described, for example, in WO 2002/072714, WO 2003/019694 and the literature cited therein.

The compounds of the invention are suitable for use in electronic devices, especially in organic electroluminescent devices (OLEDs). Depending on the substitution, the compounds are used in different functions and layers.

The compounds according to the invention can be used in any function in the organic electroluminescent device, for example as matrix material, as emitting material, as hole-transporting material or as electron-transporting material. Preference is given to use as a matrix material in an emitting layer, preferably a fluorescent emitting layer, to use as hole transport material in a hole-transporting layer of an OLED, and to use as an emitting material, preferably as a blue-fluorescing material, in an emitting layer.

The invention therefore further provides for the use of a compound of formula (I) in an electronic device. This electronic device is preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and more preferably organic electroluminescent devices (OLEDs).

The invention further provides an electronic device comprising at least one compound of the formula (I). The electronic device is preferably selected from the above-specified devices. Particular preference is given to an organic electroluminescent device comprising anode, cathode and at least one emitting layer, characterized in that at least one organic layer comprises at least one compound of formula (I). Very particular preference is given to an organic electroluminescent device comprising anode, cathode and at least one emitting layer comprising at least one compound of formula (I).

Apart from the cathode, anode and emitting layer, the organic electroluminescent device may also comprise further layers. These are selected, for example, from in each case one or more hole injection layers, hole transport layers, hole blocker layers, electron transport layers, electron injection layers, electron blocker layers, exciton blocker layers, interlayers, charge generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions.

The sequence of layers in the organic electroluminescent device is preferably as follows: anode-hole injection layer-hole transport layer-emitting layer-electron transport layer-electron injection layer-cathode. Not all the layers mentioned need be present here, and it is additionally possible for further layers to be present, for example an electron blocker layer adjoining the emitting layer on the anode side, or a hole blocker layer adjoining the emitting layer on the cathode side.

The organic electroluminescent device of the invention may contain two or more emitting layers. More preferably, these emission layers in this case have several emission maxima between 380 nm and 750 nm overall, such that the overall result is white emission; in other words, various emitting compounds which may fluoresce or phosphoresce and which emit blue or green or yellow or orange or red light are used in the emitting layers. Especially preferred are three-layer systems, i.e. systems having three emitting layers, where preferably at least one of these layers comprises at least one compound of formula (I) and where the three layers show blue, green and orange or red emission (for the basic construction see, for example, WO 2005/011013). It should be noted that, for the production of white light, rather than a plurality of colour-emitting emitter compounds, an emitter compound used individually which emits over a broad wavelength range may also be suitable. Alternatively and/or additionally, the compounds of the invention in such an organic electroluminescent device may also be present in the hole transport layer or in another layer.

The compound of the invention is especially suitable for use as matrix compound for an emitter compound, preferably a blue-emitting emitter compound, more preferably for a blue-fluorescing emitter compound.

If the compound is used as matrix compound in an emitting layer, it is preferable that it allows triplet-triplet annihilation or triplet-triplet fusion. This is understood to mean a mechanism in which two triplet states in each case combine to form one singlet state, which increases the efficiency of the singlet OLED. It is preferable, therefore, when the compound of the formula (I) is used as matrix material in the emitting layer, that the triplet levels of the materials of the layers adjoining the emitting layer are greater than that of the compound of the formula (I). It is further preferable that the triplet level of the emitting compound present together with the compound of the formula (I) in the emitting layer is higher than the triplet level of the compound of the formula (I).

If the compound of the invention is used as matrix material, it can be used in combination with any emitting compounds known to those skilled in the art. Preferably, it is used in combination with the preferred emitting compounds specified below, particularly the preferred fluorescing compounds specified below.

If the emitting layer of the organic electroluminescent device comprises a mixture of an emitting compound and a matrix compound, the following applies:

The proportion of the emitting compound in the mixture of the emitting layer is preferably between 0.1% and 50.0%, more preferably between 0.5% and 20.0%, and most preferably between 1.0% and 10.0%. Correspondingly, the proportion of the matrix material(s) is preferably between 50.0% and 99.9%, more preferably between 80.0% and 99.5%, and most preferably between 90.0% and 99.0%.

The figures for the proportions in % are understood in the context of the present application to mean % by volume when the compounds are applied from the gas phase, and to mean % by weight when the compounds are applied from solution.

In a further preferred embodiment of the invention, the compounds of the formula (I) are used as hole transport materials in a hole-transporting layer. This may be any layer arranged between anode and emitting layer, for example a hole injection layer, a hole transport layer or an electron blocker layer. It is preferably a hole transport layer, i.e. a layer between the hole injection layer and the electron blocker layer or the emitting layer.

If the compound of formula (I) is used as hole transport material in a hole transport layer, a hole injection layer or an electron blocker layer, the compound can be used as pure material, i.e. in a proportion of 100%, in the hole transport layer, or it can be used in combination with one or more further compounds. In a preferred embodiment, the organic layer containing the compound of the formula (I) then additionally contains one or more p-dopants. p-Dopants used according to the present invention are preferably those organic electron acceptor compounds capable of oxidizing one or more of the other compounds in the mixture.

If the compound of the formula (I) is used as emitting compound in an emitting layer, it is preferably a blue-fluorescing emitting compound. In this case, it is preferably used in combination with at least one further compound (matrix compound) in the emitting layer. In this case, the above-specified preferred embodiments apply to the proportions of the emitting compound of the formula (I) and the matrix compound. Preferred matrix compounds for combination with the compound of the formula (I) in its function as emitting compound are selected from the preferred classes of matrix compounds specified hereinafter.

Detailed hereinafter are general preferred material classes for use as corresponding functional materials in the organic electroluminescent devices of the invention.

Suitable phosphorescent emitting compounds are especially compounds which, when suitably excited, emit light, preferably in the visible region, and also contain at least one atom of atomic number greater than 20, preferably greater than 38, and less than 84, more preferably greater than 56 and less than 80. Preference is given to using, as phosphorescent emitting compounds, compounds containing copper, molybdenum, tungsten, rhenium, ruthenium, osmium, rhodium, iridium, palladium, platinum, silver, gold or europium, especially compounds containing iridium, platinum or copper.

In the context of the present invention, all luminescent iridium, platinum or copper complexes are considered to be phosphorescent compounds.

Examples of the above-described phosphorescent emitting compounds can be found in applications WO 2000/70655, WO 2001/41512, WO 2002/02714, WO 2002/15645, EP 1191613, EP 1191612, EP 1191614, WO 2005/033244, WO 2005/019373 and US 2005/0258742. In general, all phosphorescent complexes as used for phosphorescent OLEDs according to the prior art and as known to those skilled in the art in the field of organic electroluminescent devices are suitable for use in the devices of the invention. It is also possible for the person skilled in the art, without exercising inventive skill, to use further phosphorescent complexes in combination with the compounds of the invention in OLEDs.

Preferred fluorescent emitters are, aside from the compounds of the invention, selected from the class of the arylamines. An arylamine in the context of this invention is understood to mean a compound containing three substituted or unsubstituted aromatic or heteroaromatic ring systems bonded directly to the nitrogen. Preferably, at least one of these aromatic or heteroaromatic ring systems is a fused ring system, more preferably having at least 14 aromatic ring atoms. Preferred examples of these are aromatic anthracenamines, aromatic anthracenediamines, aromatic pyrenamines, aromatic pyrenediamines, aromatic chrysenamines or aromatic chrysenediamines. An aromatic anthracenamine is understood to mean a compound in which a diarylamino group is bonded directly to an anthracene group, preferably in the 9 position. An aromatic anthracenediamine is understood to mean a compound in which two diarylamino groups are bonded directly to an anthracene group, preferably in the 9,10 positions. Aromatic pyrenamines, pyrenediamines, chrysenamines and chrysenediamines are defined analogously, where the diarylamino groups are bonded to the pyrene preferably in the 1 position or 1,6 positions. Further preferred emitters are indenofluorenamines or -fluorenediamines, for example according to WO 2006/108497 or WO 2006/122630, benzoindenofluorenamines or -fluorenediamines, for example according to WO 2008/006449, and dibenzoindenofluorenamines or -fluorenediamines, for example according to WO 2007/140847, and the indenofluorene derivatives having fused aryl groups disclosed in WO 2010/012328. Likewise preferred are the pyrenearylamines disclosed in WO 2012/048780 and WO 2013/185871. Likewise preferred are the benzoindenofluoreneamines disclosed in WO 2014/037077, the benzofluoreneamines disclosed in WO 2014/106522 and the extended indenofluorenes disclosed in WO 2014/111269.

Preferred fluorescent emitting compounds are depicted in the following table:

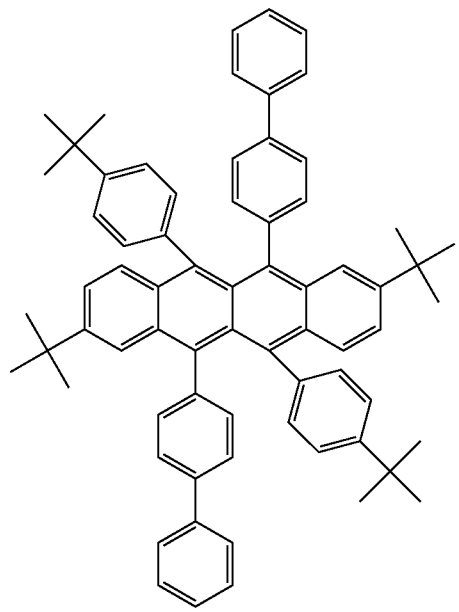 [SMILES: CC(C)(C)c1ccc(-c2c3ccc(C(C)(C)C)cc3c(-c3ccc(-c4ccccc4)cc3)c3c(-c4ccc(C(C)(C)C)cc4)c4ccc(C(C)(C)C)cc4c(-c4ccc(-c5ccccc5)cc4)c23)cc1]
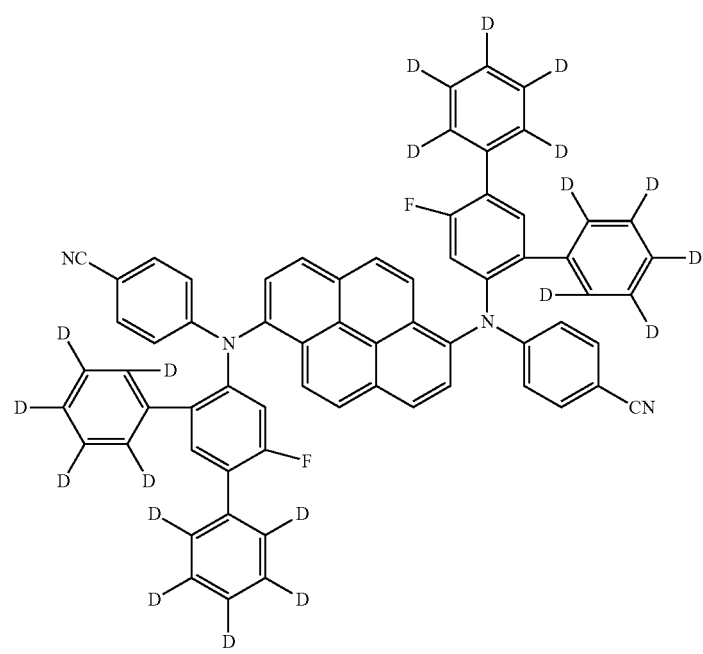 [SMILES: [2H]c1c([2H])c([2H])c(-c2cc(-c3c([2H])c([2H])c([2H])c([2H])c3[2H])c(N(c3ccc(C#N)cc3)c3ccc4ccc5c(N(c6ccc(C#N)cc6)c6cc(F)c(-c7c([2H])c([2H])c([2H])c([2H])c7[2H])cc6-c6c([2H])c([2H])c([2H])c([2H])c6[2H])ccc6ccc3c4c65)cc2F)c([2H])c1[2H]]

-continued
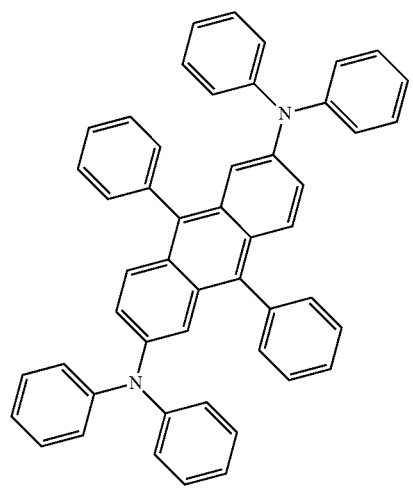 [SMILES: c1ccc(-c2c3ccc(N(c4ccccc4)c4ccccc4)cc3c(-c3ccccc3)c3ccc(N(c4ccccc4)c4ccccc4)cc23)cc1]
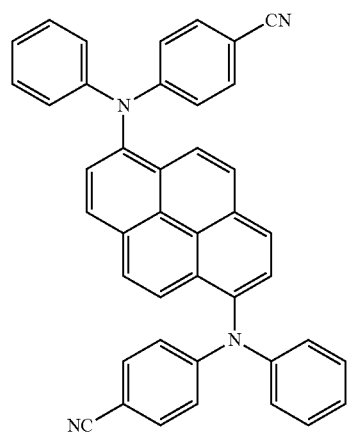 [SMILES: N#Cc1ccc(N(c2ccccc2)c2ccc3ccc4c(N(c5ccccc5)c5ccc(C#N)cc5)ccc5ccc2c3c54)cc1]
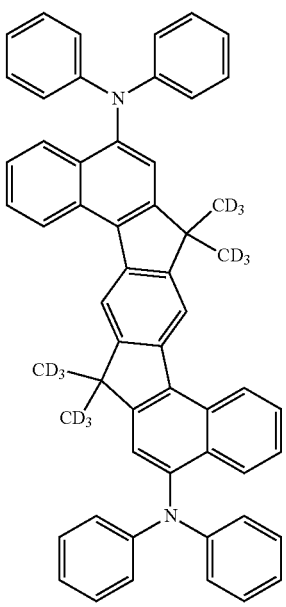 [SMILES: [2H]C([2H])([2H])C1(C([2H])([2H])[2H])c2cc3c(cc2-c2c1cc(N(c1ccccc1)c1ccccc1)c1ccccc21)C(C([2H])([2H])[2H])(C([2H])([2H])[2H])c1cc(N(c2ccccc2)c2ccccc2)c2ccccc2c1-3]

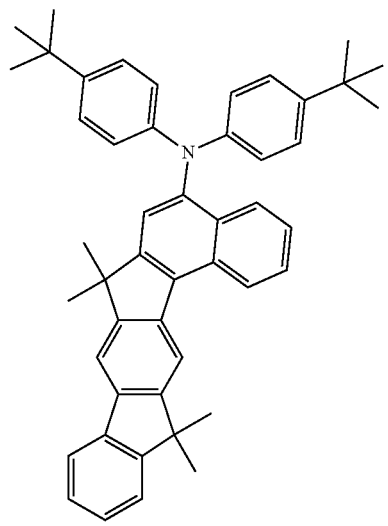 [SMILES: CC(C)(C)c1ccc(N(c2ccc(C(C)(C)C)cc2)c2cc3c(c4ccccc24)-c2cc4c(cc2C3(C)C)-c2ccccc2C4(C)C)cc1]
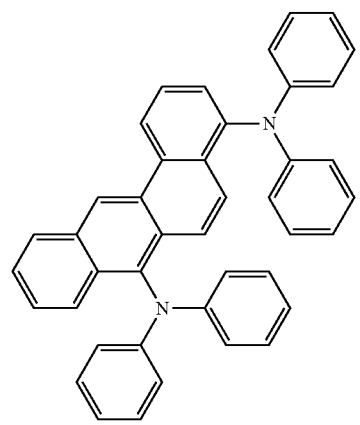 [SMILES: c1ccc(N(c2ccccc2)c2cccc3c2ccc2c(N(c4ccccc4)c4ccccc4)c4ccccc4cc23)cc1]
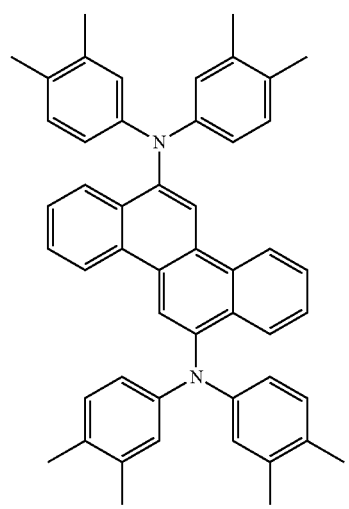

-continued
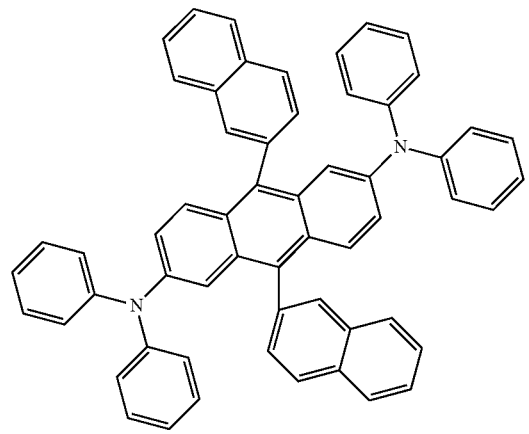 [SMILES: c1ccc(N(c2ccccc2)c2ccc3c(-c4ccc5ccccc5c4)c4cc(N(c5ccccc5)c5ccccc5)ccc4c(-c4ccc5ccccc5c4)c3c2)cc1]
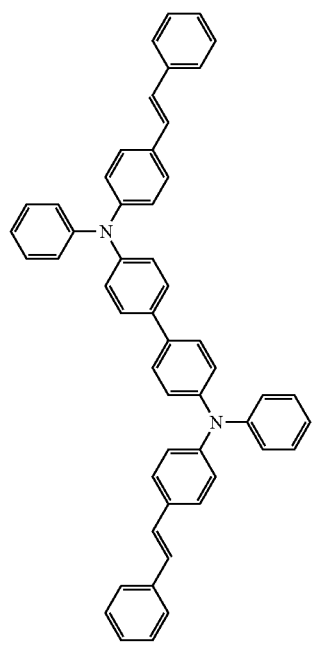 [SMILES: C(=C\c1ccc(N(c2ccccc2)c2ccc(-c3ccc(N(c4ccccc4)c4ccc(/C=C/c5ccccc5)cc4)cc3)cc2)cc1)/c1ccccc1]
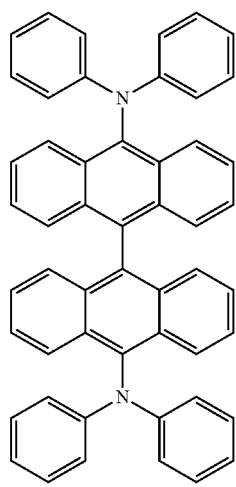 [SMILES: c1ccc(N(c2ccccc2)c2c3ccccc3c(-c3c4ccccc4c(N(c4ccccc4)c4ccccc4)c4ccccc34)c3ccccc23)cc1]

-continued
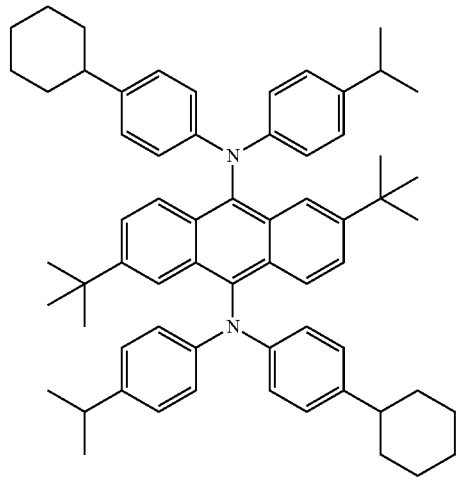 [SMILES: CC(C)c1ccc(N(c2ccc(C3CCCCC3)cc2)c2c3ccc(C(C)(C)C)cc3c(N(c3ccc(C(C)C)cc3)c3ccc(C4CCCCC4)cc3)c3ccc(C(C)(C)C)cc23)cc1]
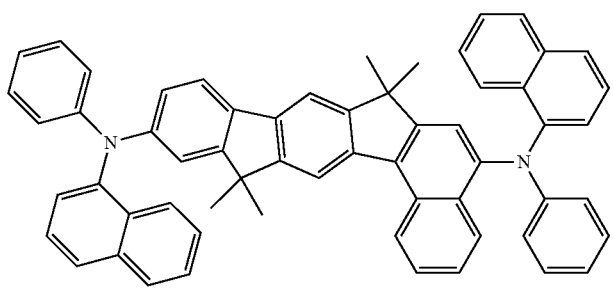 [SMILES: CC1(C)c2cc(N(c3ccccc3)c3cccc4ccccc34)ccc2-c2cc3c(cc21)-c1c(cc(N(c2ccccc2)c2cccc4ccccc24)c2ccccc12)C3(C)C]
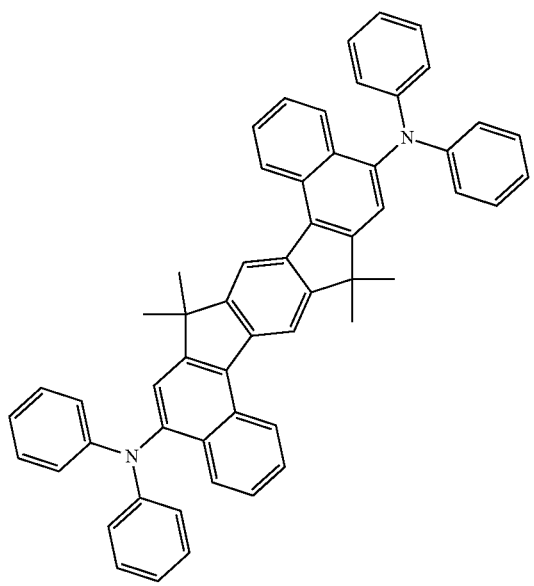 [SMILES: CC1(C)c2cc3c(cc2-c2c1cc(N(c1ccccc1)c1ccccc1)c1ccccc21)C(C)(C)c1cc(N(c2ccccc2)c2ccccc2)c2ccccc2c1-3]

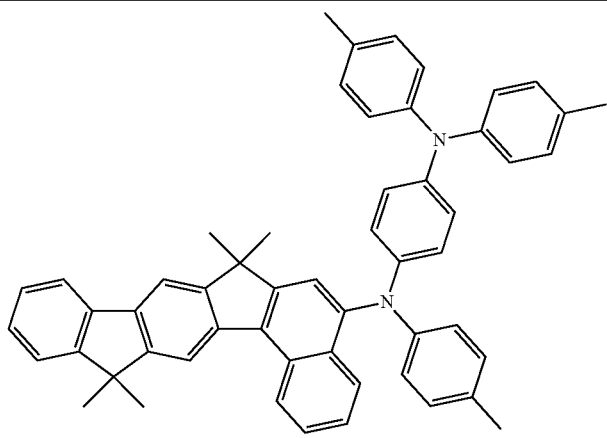
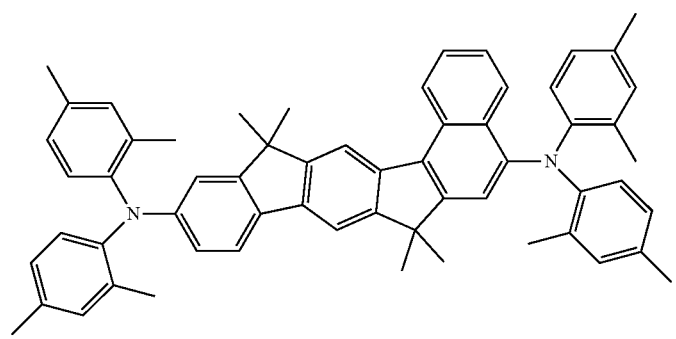
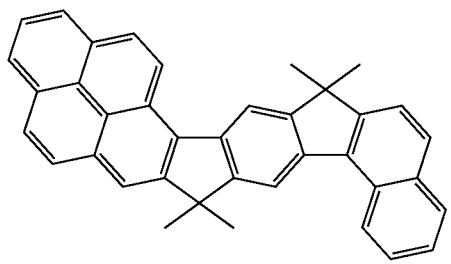 [SMILES: CC1(C)c2cc3c(cc2-c2c1ccc1ccccc21)C(C)(C)c1cc2ccc4cccc5ccc(c1-3)c2c45]
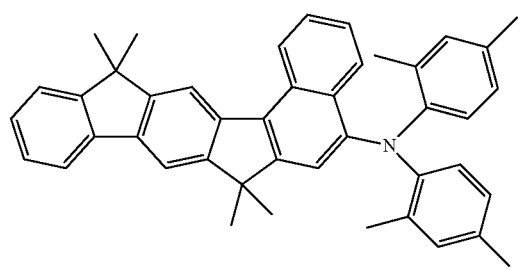 [SMILES: Cc1ccc(N(c2ccc(C)cc2C)c2cc3c(c4ccccc24)-c2cc4c(cc2C3(C)C)-c2ccccc2C4(C)C)c(C)c1]

-continued
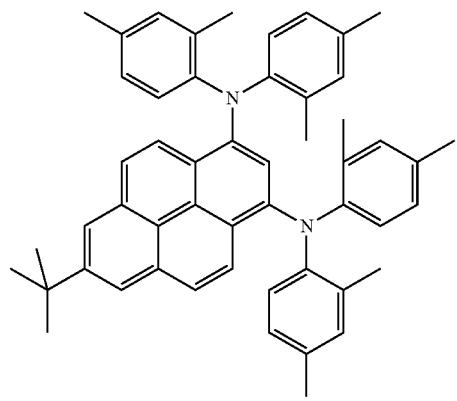 [SMILES: Cc1ccc(N(c2ccc(C)cc2C)c2cc(N(c3ccc(C)cc3C)c3ccc(C)cc3C)c3ccc4cc(C(C)(C)C)cc5ccc2c3c54)c(C)c1]
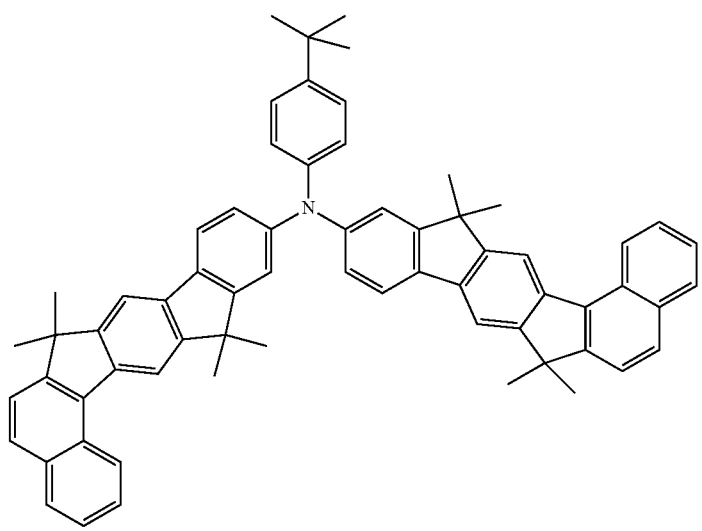 [SMILES: CC(C)(C)c1ccc(N(c2ccc3c(c2)C(C)(C)c2cc4c(cc2-3)C(C)(C)c2ccc3ccccc3c2-4)c2ccc3c(c2)C(C)(C)c2cc4c(cc2-3)C(C)(C)c2ccc3ccccc3c2-4)cc1]
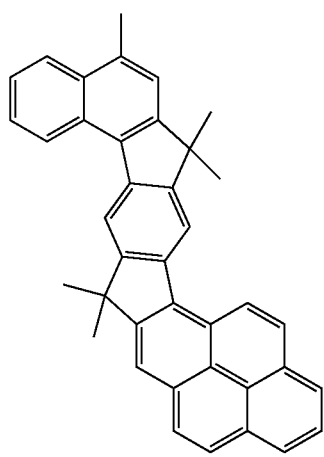 [SMILES: Cc1cc2c(c3ccccc13)-c1cc3c(cc1C2(C)C)-c1c(cc2ccc4cccc5ccc1c2c45)C3(C)C]

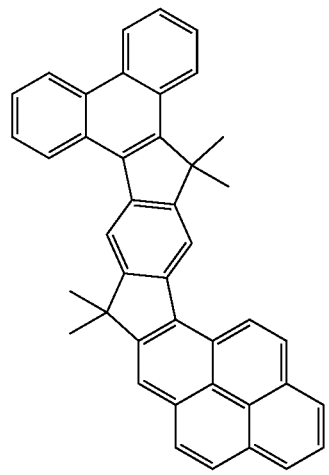 [SMILES: CC1(C)c2cc3c(cc2-c2c1cc1ccc4cccc5ccc2c1c45)C(C)(C)c1c-3c2ccccc2c2ccccc12]
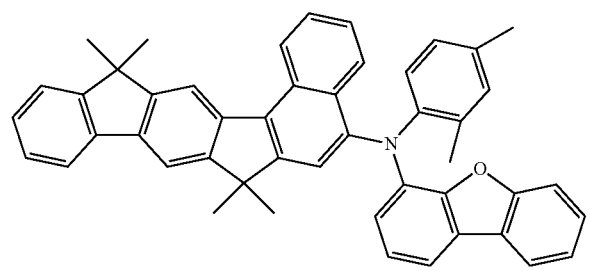 [SMILES: Cc1ccc(N(c2cc3c(c4ccccc24)-c2cc4c(cc2C3(C)C)-c2ccccc2C4(C)C)c2cccc3c2oc2ccccc23)c(C)c1]
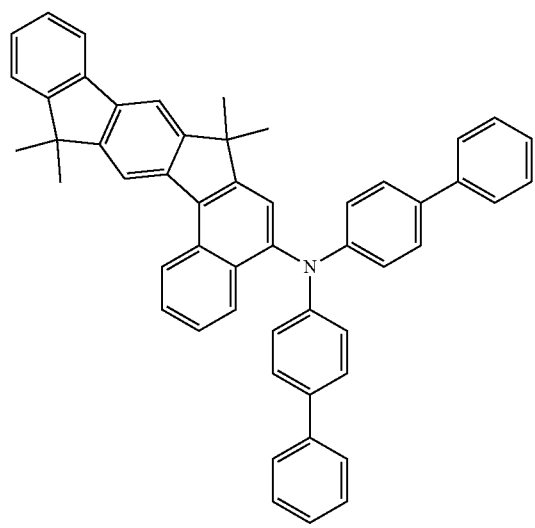 [SMILES: CC1(C)c2ccccc2-c2cc3c(cc21)-c1c(cc(N(c2ccc(-c4ccccc4)cc2)c2ccc(-c4ccccc4)cc2)c2ccccc12)C3(C)C]

-continued
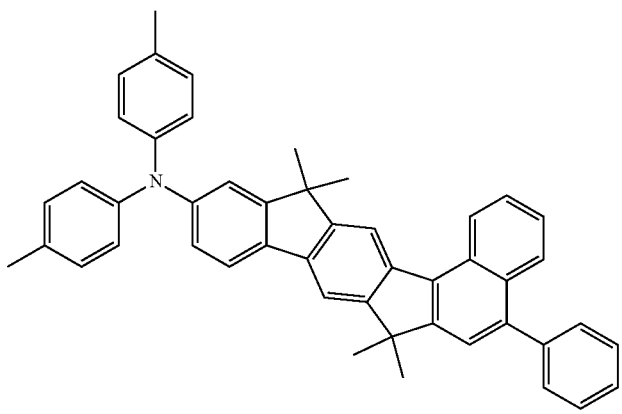 [SMILES: Cc1ccc(N(c2ccc(C)cc2)c2ccc3c(c2)C(C)(C)c2cc4c(cc2-3)C(C)(C)c2cc(-c3ccccc3)c3ccccc3c2-4)cc1]
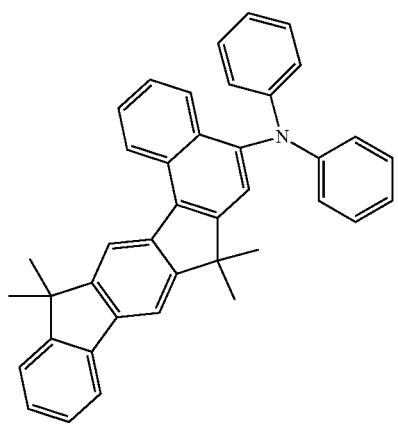 [SMILES: CC1(C)c2ccccc2-c2cc3c(cc21)-c1c(cc(N(c2ccccc2)c2ccccc2)c2ccccc12)C3(C)C]
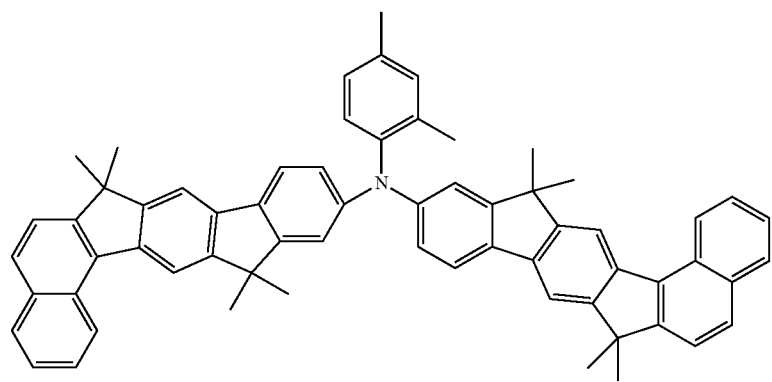 [SMILES: Cc1ccc(N(c2ccc3c(c2)C(C)(C)c2cc4c(cc2-3)C(C)(C)c2ccc3ccccc3c2-4)c2ccc3c(c2)C(C)(C)c2cc4c(cc2-3)C(C)(C)c2ccc3ccccc3c2-4)c(C)c1]

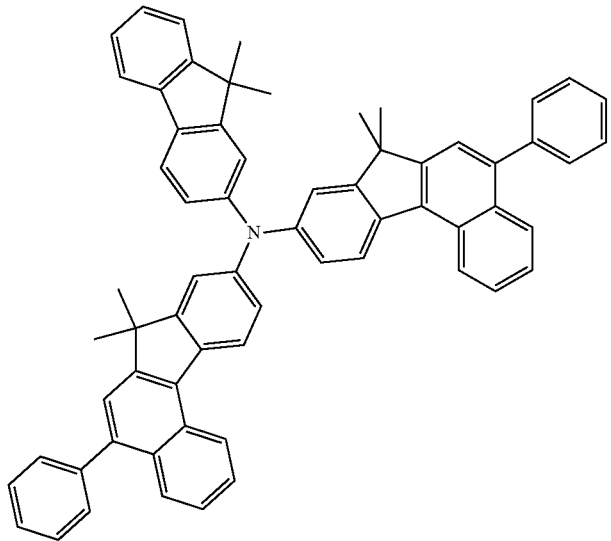 [SMILES: CC1(C)c2ccccc2-c2ccc(N(c3ccc4c(c3)C(C)(C)c3cc(-c5ccccc5)c5ccccc5c3-4)c3ccc4c(c3)C(C)(C)c3cc(-c5ccccc5)c5ccccc5c3-4)cc21]
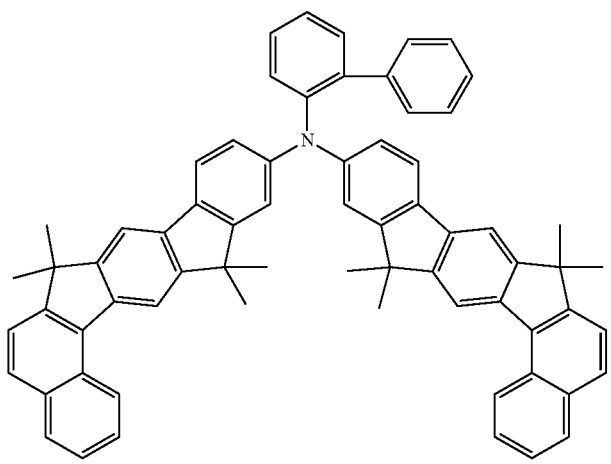 [SMILES: CC1(C)c2cc(N(c3ccc4c(c3)C(C)(C)c3cc5c(cc3-4)C(C)(C)c3ccc4ccccc4c3-5)c3ccccc3-c3ccccc3)ccc2-c2cc3c(cc21)-c1c(ccc2ccccc12)C3(C)C]
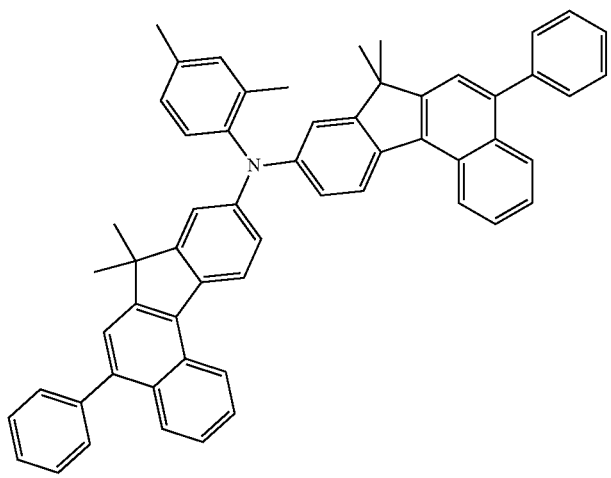 [SMILES: Cc1ccc(N(c2ccc3c(c2)C(C)(C)c2cc(-c4ccccc4)c4ccccc4c2-3)c2ccc3c(c2)C(C)(C)c2cc(-c4ccccc4)c4ccccc4c2-3)c(C)c1]

-continued
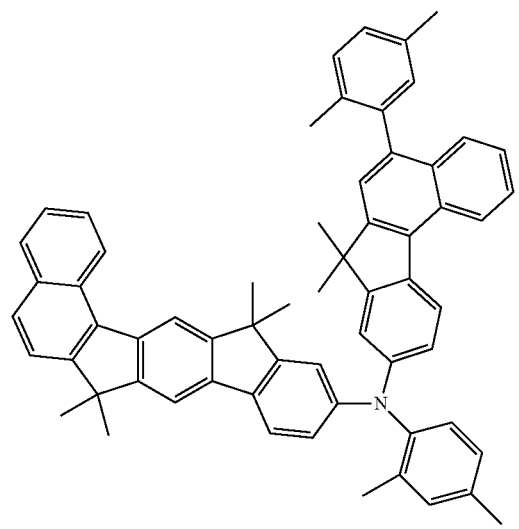 [SMILES: Cc1ccc(N(c2ccc3c(c2)C(C)(C)c2cc4c(cc2-3)C(C)(C)c2ccc3ccccc3c2-4)c2ccc3c(c2)C(C)(C)c2cc(-c4cc(C)ccc4C)c4ccccc4c2-3)c(C)c1]
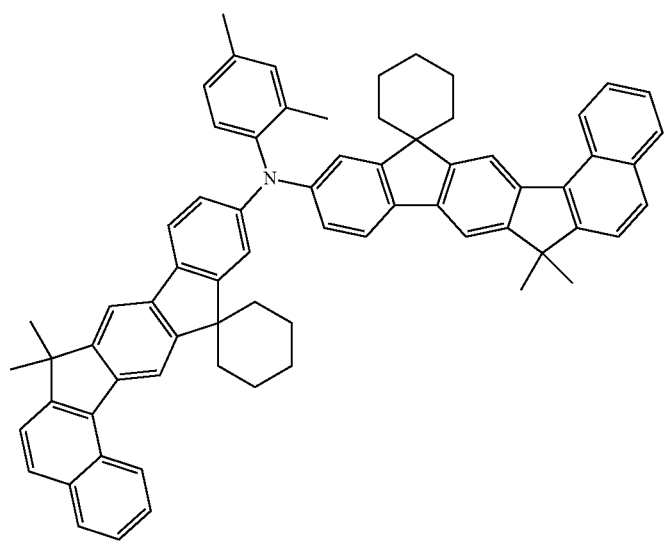 [SMILES: Cc1ccc(N(c2ccc3c(c2)C2(CCCCC2)c2cc4c(cc2-3)C(C)(C)c2ccc3ccccc3c2-4)c2ccc3c(c2)C2(CCCCC2)c2cc4c(cc2-3)C(C)(C)c2ccc3ccccc3c2-4)c(C)c1]
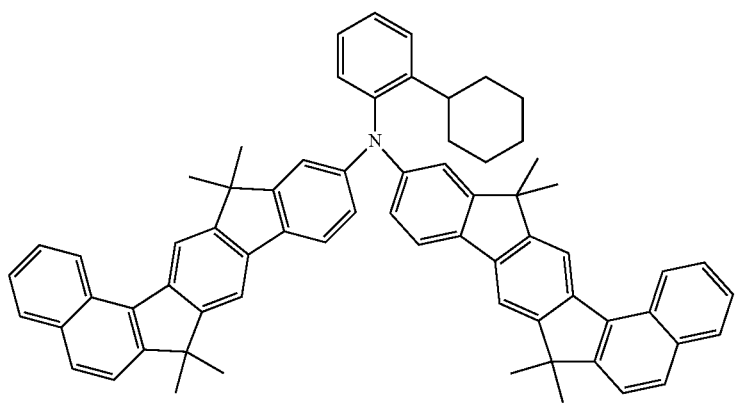 [SMILES: CC1(C)c2cc(N(c3ccc4c(c3)C(C)(C)c3cc5c(cc3-4)C(C)(C)c3ccc4ccccc4c3-5)c3ccccc3C3CCCCC3)ccc2-c2cc3c(cc21)-c1c(ccc2ccccc12)C3(C)C]

-continued
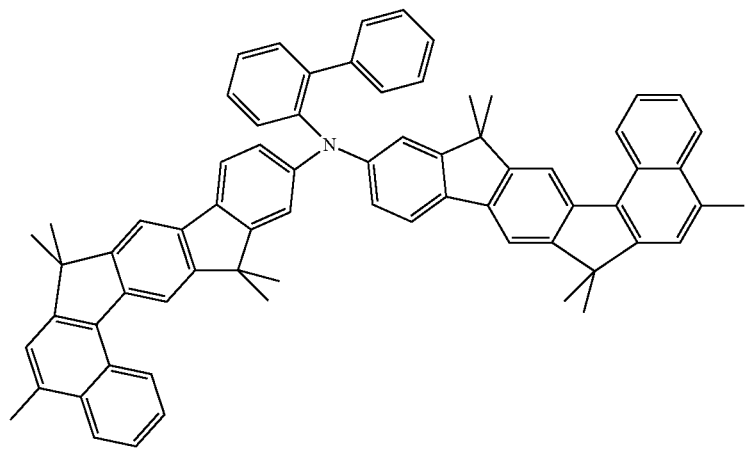
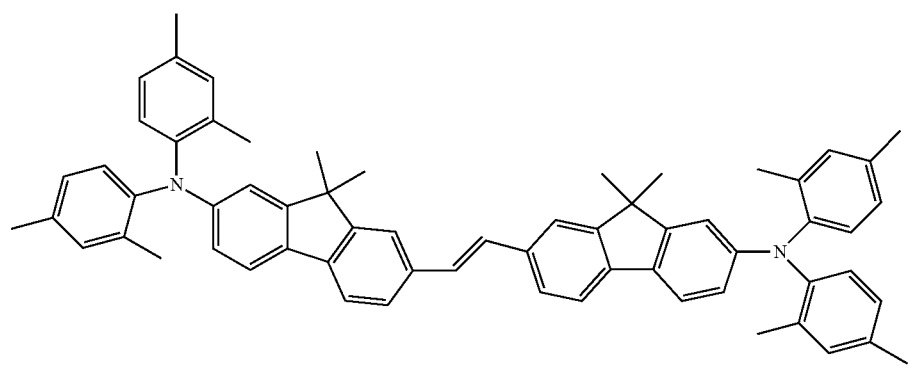
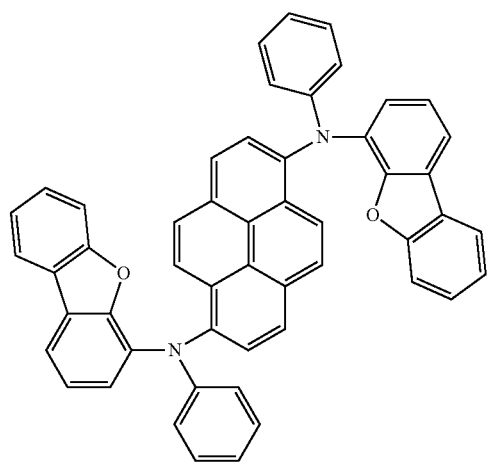 [SMILES: c1ccc(N(c2ccc3ccc4c(N(c5ccccc5)c5cccc6c5oc5ccccc56)ccc5ccc2c3c54)c2cccc3c2oc2ccccc23)cc1]

-continued
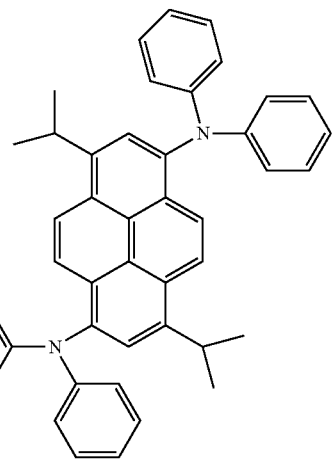
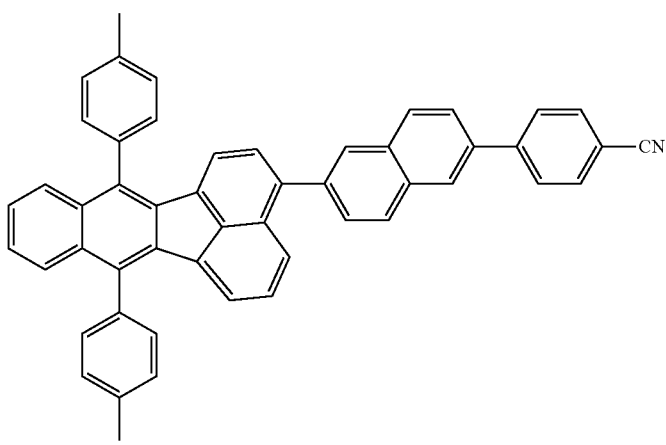 [SMILES: Cc1ccc(-c2c3c(c(-c4ccc(C)cc4)c4ccccc24)-c2ccc(-c4ccc5cc(-c6ccc(C#N)cc6)ccc5c4)c4cccc-3c24)cc1]
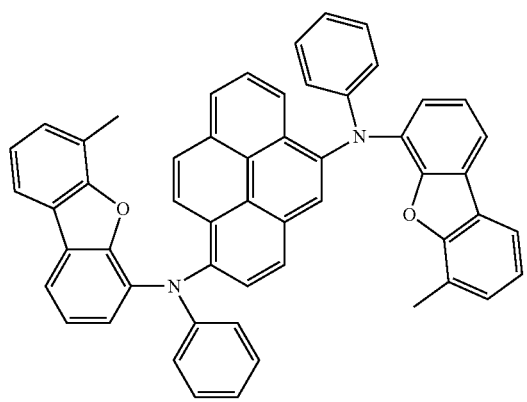 [SMILES: Cc1cccc2c1oc1c(N(c3ccccc3)c3cc4ccc(N(c5ccccc5)c5cccc6c5oc5c(C)cccc56)c5ccc6cccc3c6c45)cccc12]
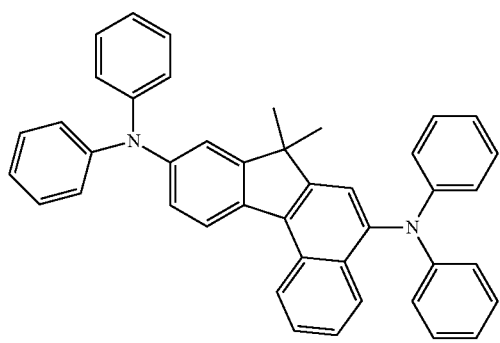 [SMILES: CC1(C)c2cc(N(c3ccccc3)c3ccccc3)ccc2-c2c1cc(N(c1ccccc1)c1ccccc1)c1ccccc21]

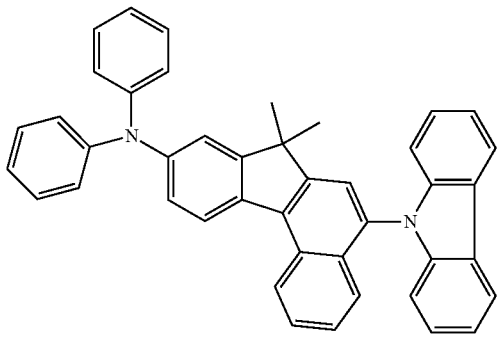 [SMILES: CC1(C)c2cc(N(c3ccccc3)c3ccccc3)ccc2-c2c1cc(-n1c3ccccc3c3ccccc31)c1ccccc21]

Preferred matrix materials for phosphorescent emitting compounds are aromatic amines, especially triarylamines, for example according to US 2005/0069729, carbazole derivatives (e.g. CBP, N,N-biscarbazolylbiphenyl) or compounds according to WO 2005/039246, US 2005/0069729, JP 2004/288381, EP 1205527 or WO 2008/086851, bridged carbazole derivatives, for example according to WO 2011/088877 and WO 2011/128017, indenocarbazole derivatives, for example according to WO 2010/136109 and WO 2011/000455, azacarbazole derivatives, for example according to EP 1617710, EP 1617711, EP 1731584, JP 2005/347160, indolocarbazole derivatives, for example according to WO 2007/063754 or WO 2008/056746, ketones, for example according to WO 2004/093207 or WO 2010/006680, phosphine oxides, sulphoxides and sulphones, for example according to WO 2005/003253, oligophenylenes, bipolar matrix materials, for example according to WO 2007/137725, silanes, for example according to WO 2005/111172, azaboroles or boronic esters, for example according to WO 2006/117052, triazine derivatives, for example according to WO 2010/015306, WO 2007/063754 or WO 2008/056746, zinc complexes, for example according to EP 652273 or WO 2009/062578, aluminium complexes, e.g. BAlq, diazasilole derivatives and tetraazasilole derivatives, for example according to WO 2010/054729, and diazaphosphole derivatives, for example according to WO 2010/054730.

Preferred matrix materials for use in combination with fluorescent emitting compounds are, aside from the compounds of the formula (I), selected from the classes of the oligoarylenes (e.g. 2,2',7,7'-tetraphenylspirobifluorene according to EP 676461 or dinaphthylanthracene), especially of the oligoarylenes containing fused aromatic groups, the oligoarylenevinylenes (e.g. DPVBi or spiro-DPVBi according to EP 676461), the polypodal metal complexes (for example according to WO 2004/081017), the hole-conducting compounds (for example according to WO 2004/058911), the electron-conducting compounds, especially ketones, phosphine oxides, sulphoxides, etc. (for example according to WO 2005/084081 and WO 2005/084082), the atropisomers (for example according to WO 2006/048268), the boronic acid derivatives (for example according to WO 2006/117052) or the benzanthracenes (for example according to WO 2008/145239). Particularly preferred matrix materials are selected from the classes of the oligoarylenes comprising naphthalene, anthracene, benzanthracene and/or pyrene or atropisomers of these compounds, the oligoarylenevinylenes, the ketones, the phosphine oxides and the sulphoxides. Very particularly preferred matrix materials are selected from the classes of the oligoarylenes comprising anthracene, benzanthracene, benzophenanthrene and/or pyrene or atropisomers of these compounds. An oligoarylene in the context of this invention shall be understood to mean a compound in which at least three aryl or arylene groups are bonded to one another.

Suitable charge transport materials as usable in the hole injection or hole transport layer or electron blocker layer or in the electron transport layer of the organic electroluminescent device of the invention are, as well as the compounds of the invention, for example, the compounds disclosed in Y. Shirota et al., Chem. Rev. 2007, 107(4), 953-1010, or other materials as used in these layers according to the prior art.

Examples of preferred hole transport materials which can be used in a hole transport, hole injection or electron blocker layer in the electroluminescent device of the invention are, aside from the compounds of the formula (I), indenofluorenamine derivatives (for example according to WO 06/122630 or WO 06/100896), the amine derivatives disclosed in EP 1661888, hexaazatriphenylene derivatives (for example according to WO 01/049806), amine derivatives having fused aromatic systems (for example according to U.S. Pat. No. 5,061,569), the amine derivatives disclosed in WO 95/09147, monobenzoindenofluoreneamines (for example according to WO 08/006449), dibenzoindenofluoreneamines (for example according to WO 07/140847), spirobifluoreneamines (for example according to WO 2012/034627 or WO 2013/120577), fluoreneamines (for example according to WO 2014/015937, WO 2014/015938 and WO 2014/015935), spirodibenzopyranamines (for example according to WO 2013/083216) and dihydroacridine derivatives (for example according to WO 2012/150001).

Preferred cathodes of the organic electroluminescent device are metals having a low work function, metal alloys or multilayer structures composed of various metals, for example alkaline earth metals, alkali metals, main group metals or lanthanoids (e.g. Ca, Ba, Mg, Al, In, Mg, Yb, Sm, etc.). Additionally suitable are alloys composed of an alkali metal or alkaline earth metal and silver, for example an alloy composed of magnesium and silver. In the case of multilayer structures, in addition to the metals mentioned, it is also possible to use further metals having a relatively high work function, for example Ag or Al, in which case combinations of the metals such as Ca/Ag, Mg/Ag or Ba/Ag, for example, are generally used. It may also be preferable to introduce a thin interlayer of a material having a high dielectric constant between a metallic cathode and the organic semiconductor. Examples of useful materials for this purpose are alkali metal or alkaline earth metal fluorides, but also the corresponding oxides or carbonates (e.g. LiF, $Li_2O$, $BaF_2$, MgO, NaF, CsF, $Cs_2CO_3$, etc.). It is also possible to use lithium quinolinate (LiQ) for this purpose. The layer thickness of this layer is preferably between 0.5 and 5 nm.

Preferred anodes are materials having a high work function. Preferably, the anode has a work function of greater than 4.5 eV versus vacuum. Firstly, metals having a high redox potential are suitable for this purpose, for example Ag, Pt or Au. Secondly, metal/metal oxide electrodes (e.g. Al/Ni/NiO$_x$, Al/PtO$_x$) may also be preferred. For some applications, at least one of the electrodes has to be transparent or partly transparent in order to enable the irradiation of the organic material (organic solar cell) or the emission of light (OLED, 0-LASER). Preferred anode materials here are conductive mixed metal oxides. Particular preference is given to indium tin oxide (ITO) or indium zinc oxide (IZO). Preference is further given to conductive doped organic materials, especially conductive doped polymers.

The device is appropriately (according to the application) structured, contact-connected and finally sealed, since the lifetime of the devices of the invention is shortened in the presence of water and/or air.

In a preferred embodiment, the organic electroluminescent device of the invention is characterized in that one or more layers are coated by a sublimation process. In this case, the materials are applied by vapour deposition in vacuum sublimation systems at an initial pressure of less than $10^{-5}$ mbar, preferably less than $10^{-6}$ mbar. In this case, however, it is also possible that the initial pressure is even lower, for example less than $10^{-7}$ mbar.

Preference is likewise given to an organic electroluminescent device, characterized in that one or more layers are coated by the OVPD (organic vapour phase deposition) method or with the aid of a carrier gas sublimation. In this case, the materials are applied at a pressure between $10^{-5}$ mbar and 1 bar. A special case of this method is the OVJP (organic vapour jet printing) method, in which the materials are applied directly by a nozzle and thus structured (for example, M. S. Arnold et al., *Appl. Phys. Lett.* 2008, 92, 053301).

Preference is additionally given to an organic electroluminescent device, characterized in that one or more layers are produced from solution, for example by spin-coating, or by any printing method, for example screen printing, flexographic printing, nozzle printing or offset printing, but more preferably LITI (light-induced thermal imaging, thermal transfer printing) or inkjet printing.

It is further preferable that an organic electroluminescent device of the invention is produced by applying one or more layers from solution and one or more layers by a sublimation method.

Because of the good solubility of the compounds of formula (I), it is preferable that the layer comprising one or more compounds of the formula (I) is applied from solution. This is preferably the emitting layer of an organic electroluminescent device.

According to the invention, the electronic devices comprising one or more compounds of the invention can be used in displays, as light sources in lighting applications and as light sources in medical and/or cosmetic applications (e.g. light therapy).

WORKING EXAMPLES

A) Synthesis Examples

A-1) Synthesis of the Base Skeleton of the Compounds

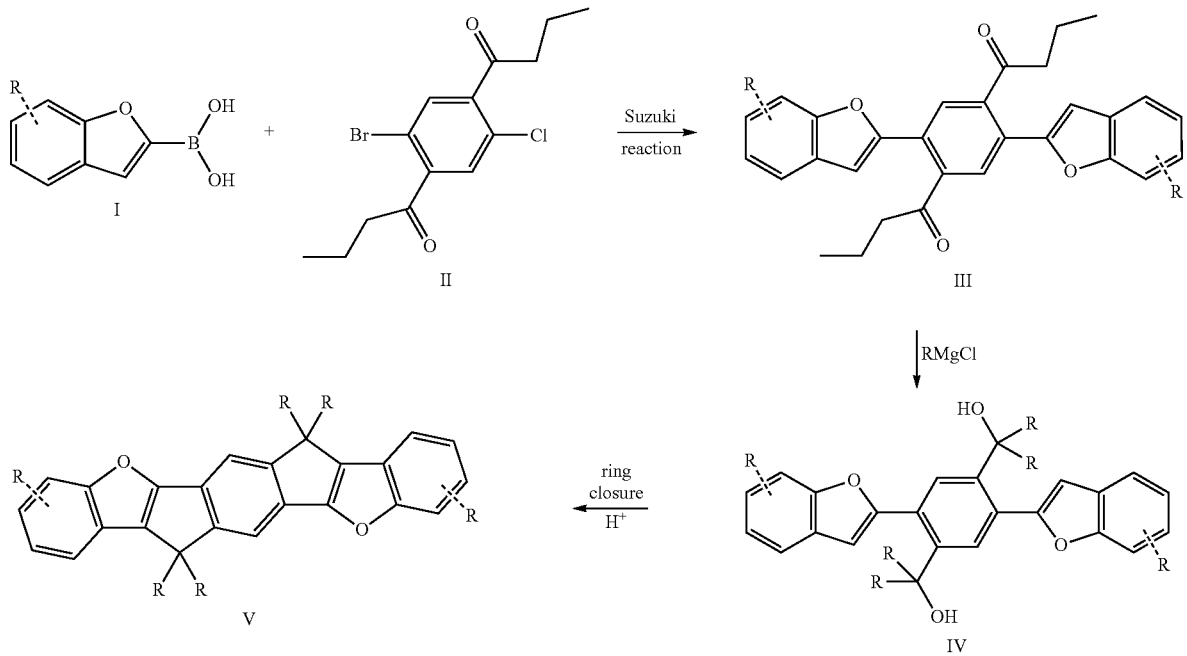

A-1-1) Synthesis of Compound I

The compound with R=H (Ia) is commercially available. Analogous compounds with R≠H, if they are not commercially available, are obtainable by the following method or by methods described in WO 2012/165612 A1, A. S. K. Hashmi, Tetrahedron, 65 (2009) 9021-9029, or Org. Biomol. Chem. 2014, 12, 4747-4753:

When R≠H, for example the compound Ib specified below, the synthesis is conducted as follows:

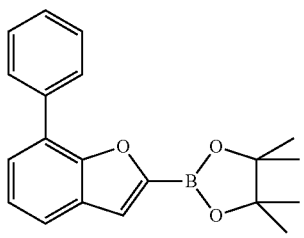 [SMILES: CC1(C)OB(c2cc3cccc(-c4ccccc4)c3o2)OC1(C)C]

Ib

A-1-1-1) General Scheme for Synthesis of Compounds of the I Type

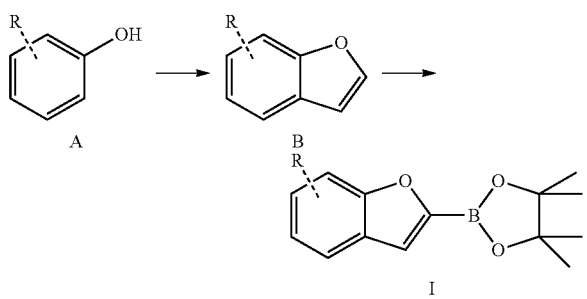

A-1-1-2) Specific Method of Preparing the Compound Ib

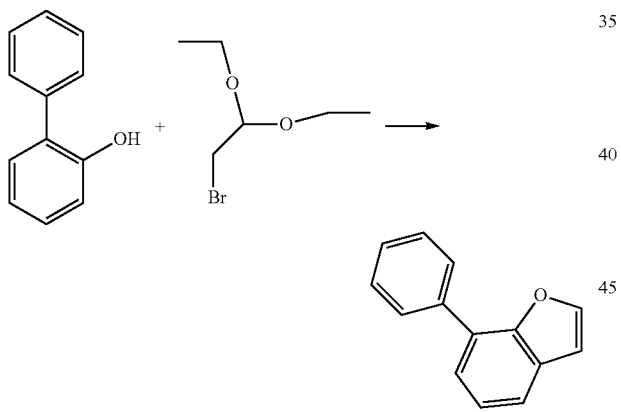

A 500 ml two-neck flask is initially charged with 35 g (206 mmol) of biphenyl-2-ol, 85.3 g (617 mmol) of potassium carbonate and 47 ml (308 mmol) of 2-bromo-1,1-diethoxyethane in 200 ml of anhydrous DMF and the mixture is refluxed for 16 hours until conversion is complete. Subsequently, the reaction is cooled down to room temperature and 400 ml of water are added. The organic phase is extended with 300 ml of toluene. The phases are separated and the aqueous phase is extracted twice with 200 ml of toluene. The combined organic phases are washed three times with 20% sodium hydroxide solution, filtered through silica gel and concentrated to dryness under reduced pressure. The residue is dissolved in 600 ml of anhydrous toluene and initially charged in a 1 l two-neck flask with a water separator, 5 g of Amberlyst 15 are added and the mixture is stirred at 125° C. for 15 hours. After cooling to room temperature, the reaction mixture is filtered and concentrated under reduced pressure. After purification by column chromatography (heptane/toluene 9:1), 31 g (160 mmol; 78% of theory) of colourless oil are obtained.

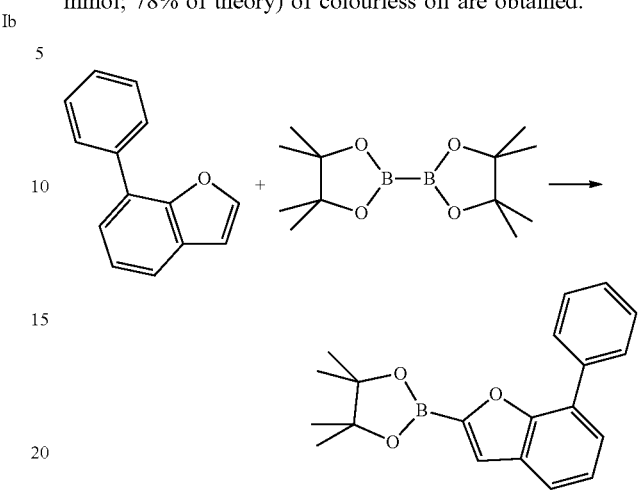

A 1 l two-neck flask is initially charged with 36 g (185 mmol) of the compound obtained above and 24.7 g (97 mmol) of bis(pinacolato)diboron in 400 ml of heptane. Subsequently, 123 mg (0.19 mmol) of (1,5-cyclooctadiene)(methoxy)iridium(I) dimer and 99.5 mg (037 mmol) of 4,4'-di-tert-butyl-2,2'-dipyridyl are added and the mixture is stirred at 35° C. for 16 h. The precipitated solid is filtered off with suction and washed with heptane and dried under reduced pressure. Yield: 51 g (159 mmol; 86% of theory) of colourless solid.

A-1-2) Synthesis of III Using the Example of Diethyl 2,5-bis(benzofuran-2-yl)terephthalate (Ar=H) (IIIa)

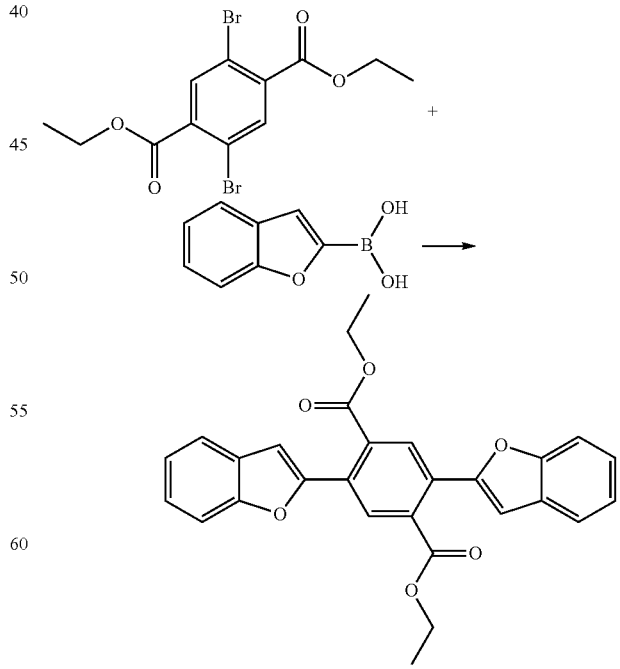

A 2 l four-neck flask is initially charged with 35 g (0.09 mol) of diethyl 2,5-dibromoterephthalate, 33.5 g (0.2 mol)

of benzofuran-2-ylboronic acid and 46.9 g (0.19 mol) of tripotassium phosphate monohydrate in 800 ml of toluene/dioxane/water (2:1:1). After adding 413 mg (1.8 mmol) of palladium acetate and 3.36 g (11 mmol), the mixture is refluxed for one hour. Subsequently, the reaction is cooled down to room temperature and the organic phase is extended with ethyl acetate. The phases are separated and the aqueous phase is extracted twice with 300 ml of ethyl acetate. The combined organic phases are washed with water, dried over sodium sulphate, filtered and concentrated under reduced pressure. The residue is admixed with 400 ml of methanol and stirred at 60° C. for 20 minutes. After cooling to room temperature, the solids are filtered and dried under reduced pressure. Yield: 40.9 g (0.09 mol, 98%) of yellow solid.

In an analogous manner, it is also possible to prepare the following compounds:

| Reactant 1 | Reactant 2 | Product | Yield |
|---|---|---|---|
| IIIa (CAS 18013-97-3) | benzofuran-2-ylboronic acid | diethyl 2,5-bis(benzofuran-2-yl)terephthalate | 98% |
| IIIb | 7-phenylbenzofuran-2-yl boronic acid pinacol ester | diethyl 2,5-bis(7-phenylbenzofuran-2-yl)terephthalate | 91% |

A-1-3) Synthesis of IV Using the Example of 2-[2,5-bis(benzofuran-2-yl)-4-(1-hydroxy-1-methylethyl)phenyl]propan-2-ol (Ar=H) (IVa)

A 4 l four-neck flask is initially charged with 46.6 g (0.2 mol) of anhydrous cerium chloride in 300 ml of anhydrous THF and cooled to 0° C. Subsequently, 40.9 g (0.09 mol) of diethyl 2,5-bis(benzofuran-2-yl)terephthalate, dissolved in 700 ml of anhydrous THF, are slowly added dropwise thereto, in such a way that the internal temperature remains below 5° C. On completion of addition, the mixture is stirred at this temperature for one hour. On completion of conversion, 400 ml of saturated ammonium chloride solution are added dropwise thereto, such that the temperature remains below 20° C. The suspension obtained is filtered and the solids are washed with ethyl acetate. The filtrate is washed thoroughly with ethyl acetate and then the phases are separated. The aqueous phase is extracted twice with ethyl acetate (200 ml). The combined organic phases are dried over sodium sulphate and then concentrated under reduced pressure. After adding 400 ml of heptane, the mixture is then stirred at 60° C. for 30 minutes. The desired product precipitates out as a pale yellow solid. Yield: 35 g (82 mmol, 92%)

In an analogous manner, it is also possible to prepare the following compounds:

| | Reactant 1 | Reactant 2 | Product | Yield |
|---|---|---|---|---|
| IVa | (structure) | MeMgCl | (structure) | 92% |
| IVb | (structure) | MeMgCl | (structure) | 79% |

A-1-4) Synthesis of V Using the Example of Ar=H (Va)

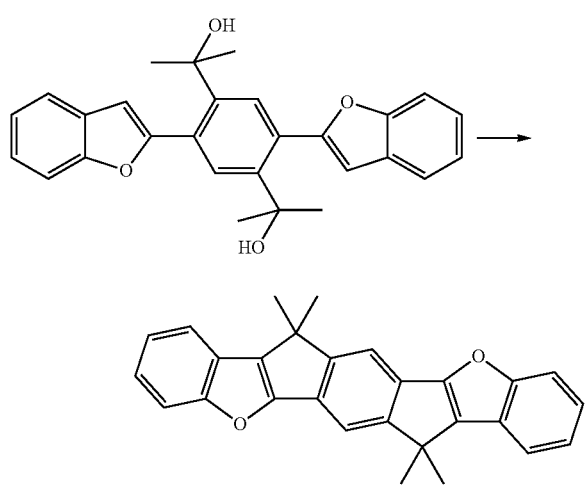

A 2 l four-neck flask is initially charged with 24 g (0.25 mol) of polyphosphoric acid in 200 ml of dichloromethane and cooled to 0° C. At this temperature, 16 ml of methanesulphonic acid are added dropwise. Subsequently, 35 g (0.08 mol) of IVa, dissolved in 900 ml of dichloromethane, are slowly added dropwise at 0° C. and stirring is continued at this temperature for two hours. On completion of conversion, the reaction is admixed with 100 ml of ethanol and stirred for 30 minutes. A further 700 ml of ethanol are added to the reaction mixture and the dichloromethane is removed under reduced pressure. The precipitated solid is filtered. The further purification is effected by means of hot extraction over aluminium oxide with toluene/heptane 1:2 and repeated recrystallization from heptane/toluene. After sublimation twice at $10^{-5}$ bar and >250° C., the product is obtained in an HPLC purity of >99.9%. Yield: 8.4 g (22 mmol; 27%) of pale yellow solid.

In an analogous manner, it is possible to prepare the following compounds:

| Reactant 1 | Product | Yield |
|---|---|---|
| Va 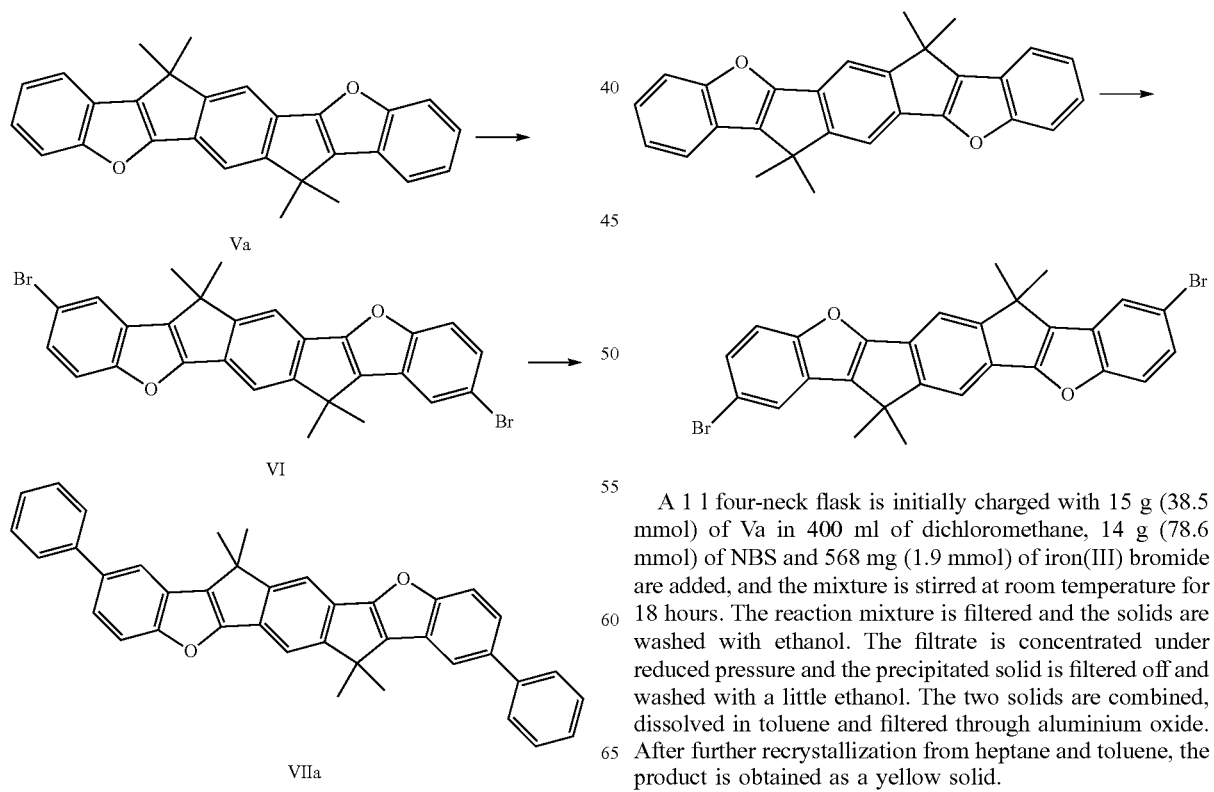 | | 27% |
| Vb | | 52% |

A-2) Introduction of Substituents in the Base Skeleton of the Compound by Bromination and Suzuki Reaction A-2-1) Bromination of Va Using the Example of VI A 1 l four-neck flask is initially charged with 15 g (38.5 mmol) of Va in 400 ml of dichloromethane, 14 g (78.6 mmol) of NBS and 568 mg (1.9 mmol) of iron(III) bromide are added, and the mixture is stirred at room temperature for 18 hours. The reaction mixture is filtered and the solids are washed with ethanol. The filtrate is concentrated under reduced pressure and the precipitated solid is filtered off and washed with a little ethanol. The two solids are combined, dissolved in toluene and filtered through aluminium oxide. After further recrystallization from heptane and toluene, the product is obtained as a yellow solid.

Yield: 11.7 g (21 mmol; 56%)

A-2-2) Synthesis of VIIa

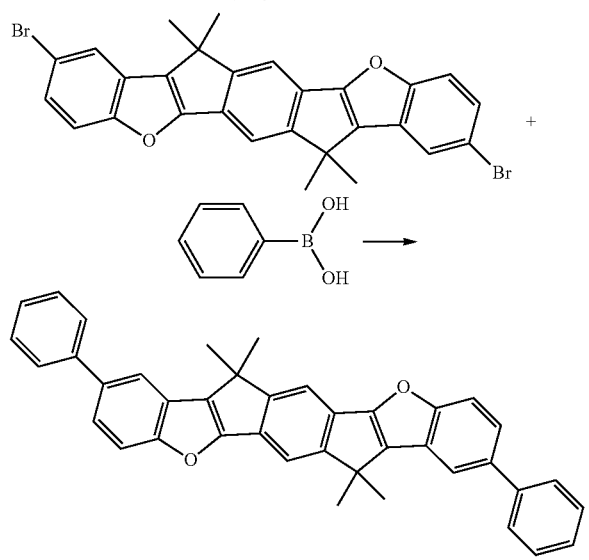

A 1 l four-neck flask is initially charged with 20 g (36 mmol) of VIa, 10 g (82 mmol) of phenylboronic acid and 18.6 g (81 mmol) of tripotassium phosphate monohydrate in 600 ml of toluene/dioxane/water (1:1:1). Subsequently, 161 mg (0.72 mmol) of palladium acetate and 1.3 g (4.32 mmol) of tri-o-tolylphosphine are added and the mixture is refluxed for 16 h until conversion is complete. After cooling to room temperature, the organic phase is extended with 300 ml of ethyl acetate and the phases are separated. The aqueous phase is extracted twice with ethyl acetate. The combined organic phases are dried over sodium sulphate and then concentrated under reduced pressure. Subsequently, the solid obtained is hot-extracted over aluminium oxide (toluene/heptane). The precipitated solid is filtered and recrystallized repeatedly from toluene/heptane. After sublimation twice ($10^{-6}$ bar, >300° C.), the product is obtained as a pale yellow solid with an HPLC purity of >99.9%. Yield: 9.3 g (17 mmol; 48%).

In an analogous manner, it is possible to prepare the following compounds:

| | Reactant 1 | Reactant 2 | Product VII | Yield |
|---|---|---|---|---|
| VIIa | Ph—B(OH)₂ | VI | | 48% |
| VIIb | Naphthyl—B(OH)₂ | VI | | 37% |
| VIIc | o-Tolyl—B(OH)₂ | VI | | 46% |

| Reactant 1 | Reactant 2 | Product VII | Yield |
|---|---|---|---|
| VIId 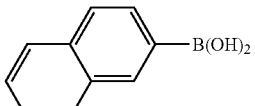 | VI | 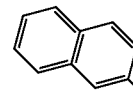 | 43% |
| VIIe 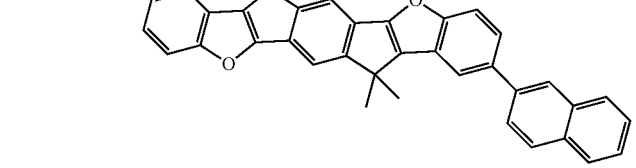 | VI | 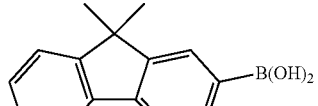 | 49% |
| VIIf 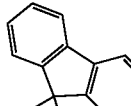 | VI | 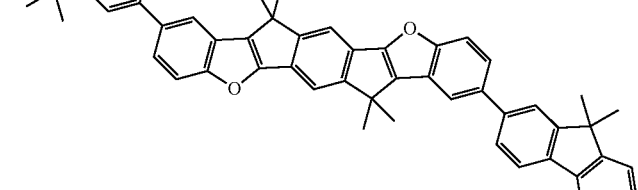 | 47% |

B) Device Examples

OLEDs of the invention and OLEDs according to the prior art are produced by a general method according to WO 04/058911, which is adapted to the circumstances described here (variation in layer thickness, materials).

In the examples which follow (see tables 1 to 3), the data of various OLEDs are presented. Substrates used are glass substrates coated with structured ITO (indium tin oxide) of thickness 50 nm. The OLEDs basically have the following layer structure: substrate/buffer/hole injection layer 1 (95% HTL1+5% HIL, 20 nm)/hole transport layer (HTL2, thickness stated in Table 1)/emission layer (EML, 20 nm)/electron transport layer (ETL, 20 nm)/electron injection layer (EIL, 3 nm) and finally a cathode. The cathode is formed by an aluminium layer of thickness 100 nm. The buffer applied by spin-coating is a 20 nm-thick layer of Clevios P VP Al 4083 (sourced from Heraeus Clevios GmbH, Leverkusen). All the rest of the materials are applied by thermal vapour deposition in a vacuum chamber. The structure of the OLEDs is shown in Table 1. The materials used are shown in Table 3.

The emission layer (EML) always consists of at least one matrix material (host=H) and an emitting compound (dopant=D) which is added to the matrix material in a particular proportion by volume by co-evaporation. Details given in such a form as H1:D1 (95%:5%) mean here that the material H1 is present in the layer in a proportion by volume of 95% and D1 in a proportion of 5%.

The OLEDs are characterized in a standard manner. For this purpose, the electroluminescence spectra are recorded, and the current efficiency (measured in cd/A) and the external quantum efficiency (EQE, measured in percent) are calculated as a function of luminance, assuming Lambertian radiation characteristics, from current-voltage-luminance characteristics (IUL characteristics). The electroluminescence spectra are recorded at a luminance of 1000 cd/m$^2$, and the CIE 1931 x and y colour coordinates are calculated therefrom. The parameter EQE @ 1000 cd/m$^2$ refers to the external quantum efficiency at an operating luminance of 1000 cd/m$^2$. The data obtained for the various OLEDs are collated in Table 2.

Use of the Compounds of the Invention as Matrix in Fluorescent OLEDs

The compounds of the invention H1 and H2 are used individually as matrix in the emitting layer of OLEDs (for structure see Table 3). The emitter material used in the emitting layer is the compound D. The OLEDs obtained are I1 and I2. They exhibit very good external quantum efficiencies (EQEs) with deep blue emission (Table 2).

Use of the Compounds of the Invention as Hole Transport Materials in OLEDs

Example I3, in which the compound of the invention H1 is used as hole transport material in the hole transport layer, likewise shows good external quantum efficiency with deep blue emission (Table 2). This demonstrates the good suitability of the compounds of the invention as hole-transporting compounds.

TABLE 1
Structure of the OLEDs
| Ex. | HTL (20 nm) | EML (thickness/20 nm) |
|---|---|---|
| I1 | HTL2 | H-1(95%):D(5%) |
| I2 | HTL2 | H-2(95%):D(5%) |
| I3 | H-1 | BH (95%):D(5%) |
TABLE 2
Data of the OLEDs
| Ex. | EQE [%] @ 1000 cd/m$^2$ | CIE x | CIE y |
|---|---|---|---|
| I1 | 6.3 | 0.139 | 0.143 |
| I2 | 6.5 | 0.142 | 0.135 |
| I3 | 5.7 | 0.142 | 0.158 |
TABLE 3
Structures of the materials used
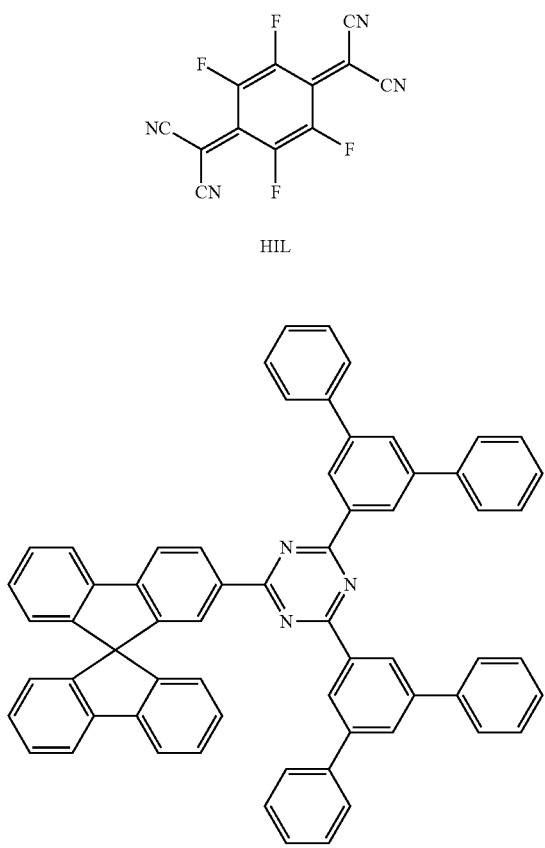
HIL
ETL
TABLE 3-continued
Structures of the materials used
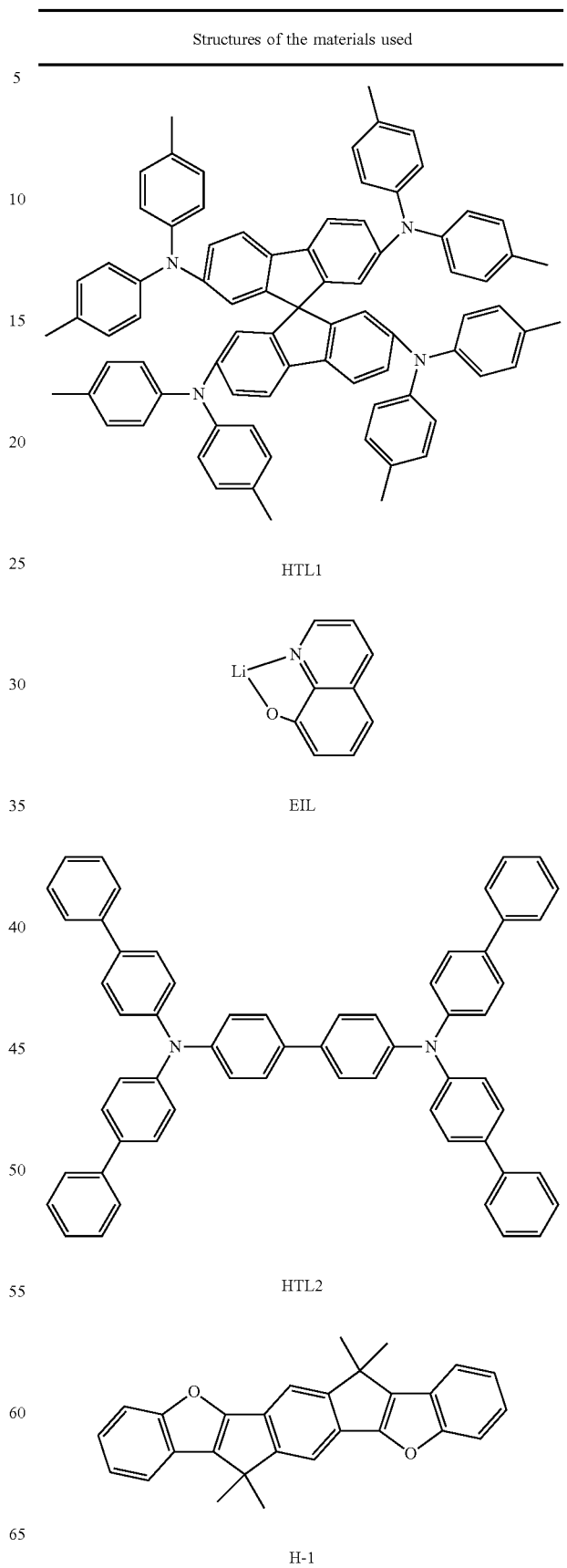
HTL1
EIL
HTL2
H-1

TABLE 3-continued

Structures of the materials used

H-2

D

BH

The invention claimed is:

1. A compound of formula (I):

$$\boxed{Ar^3}\boxed{Ar^2}\boxed{Ar^1}\boxed{Ar^2}\boxed{Ar^3} \quad (I)$$

wherein $\boxed{Ar^1}$ is a benzene ring optionally substituted in each instance by one or more radicals $R^1$;

$\boxed{Ar^2}$ is the same or different in each instance and is selected from the group consisting of units of formulae (Ar²-1) or (Ar²-2)

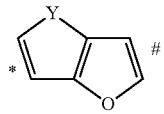 (Ar²-1)

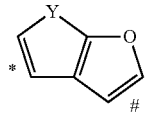 (Ar²-2)

wherein
the bond denoted with * is the bond via which the unit is fused to the $Ar^1$ group, and
the bond denoted with # is the bond via which the unit is fused to the $Ar^a$ group;
Y is the same or different in each instance and is $C(R^2)_2$ or $Si(R^2)_2$;

is the same or different in each instance and is selected from the group consisting of aromatic ring systems having 6 to 30 aromatic ring atoms and heteroaromatic ring systems having 5 to 30 aromatic ring atoms, each of which is optionally substituted by radicals $R^3$;

$R^1$, $R^2$, and $R^3$
are the same or different in each instance and are selected from H, D, F, C(=O)R⁴, CN, Si(R⁴)₃, N(R⁴)₂, P(=O)(R⁴)₂, OR⁴, S(=O)R⁴, S(=O)₂R⁴, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; wherein two or more radicals $R^1$, $R^2$, and/or $R^3$ are optionally bonded to one another and optionally define a ring; and wherein the alkyl, alkoxy, alkenyl, and alkynyl groups and the aromatic and heteroaromatic ring systems are each optionally substituted by one or more radicals $R^4$; and wherein one or more CH₂ groups in the alkyl, alkoxy, alkenyl, and alkynyl groups are optionally replaced by —R⁴C=CR⁴—, —C≡C—, Si(R⁴)₂, C=O, C=NR⁴, —C(=O)O—, —C(=O)NR⁴—, NR⁴, P(=O)(R⁴), —O—, —S—, SO, or SO₂;

$R^4$ is the same or different in each instance and is selected from H, D, F, C(=O)R⁵, CN, Si(R⁵)₃, N(R⁵)₂, P(=O)(R⁵)₂, OR⁵, S(=O)R⁵, S(=O)₂R⁵, straight-chain alkyl or alkoxy groups having 1 to 20 carbon atoms, branched or cyclic alkyl or alkoxy groups having 3 to 20 carbon atoms, alkenyl or alkynyl groups having 2 to 20 carbon atoms, aromatic ring systems having 6 to 40 aromatic ring atoms, and heteroaromatic ring systems having 5 to 40 aromatic ring atoms; wherein two or more radicals $R^4$ are optionally bonded to one another and optionally define a ring; wherein the alkyl, alkoxy, alkenyl, and alkynyl groups and the aromatic and heteroaromatic ring systems are each optionally substituted by one or more radicals $R^5$; and wherein one or more CH₂ groups in the alkyl, alkoxy, alkenyl, and alkynyl groups are optionally replaced by —R⁵C═CR⁵—, —C≡C—, Si(R⁵)₂, C═O, C═NR⁵, —C(═O)O—, —C(═O)NR⁵—, NR⁵, P(═O)(R⁵), —O—, —S—, SO or SO₂;

R⁵ is the same or different in each instance and is selected from H, D, F, CN, alkyl groups having 1 to 20 carbon atoms, aromatic ring systems having 6 to 40 aromatic ring atoms, and heteroaromatic ring systems having 5 to 40 aromatic ring atoms; wherein two or more radicals R⁵ are optionally bonded to one another and optionally define a ring; and wherein the alkyl groups, aromatic ring systems, and heteroaromatic ring systems are optionally substituted by F or CN.

2. The compound of claim 1, wherein the compound is a compound of formula (I-C):

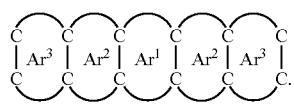     (I-C)

3. The compound of claim 1, wherein the compound is symmetric with respect to a mirror plane through the middle and at right angles to the longitudinal axis of the elongated molecule.

4. The compound of claim 1, wherein Ar¹ is a group of formulae (Ar¹-1) or (Ar¹-2):

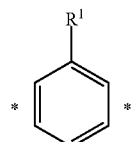     (Ar¹-1)

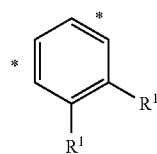     (Ar¹-2)

wherein the bonds denoted with * are the bonds via which the Ar¹ group is fused to the two adjacent Ar² groups.

5. The compound of claim 1, wherein Ar² is a group of formula (Ar²-1).

6. The compound of claim 1, wherein Y is C(R²)₂.

7. The compound of claim 1, wherein Ar³ is the same or different in each instance and is selected from the following groups:

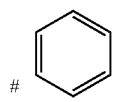     (Ar³-1)

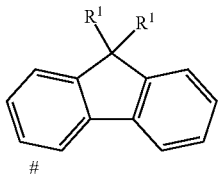     (Ar³-2)

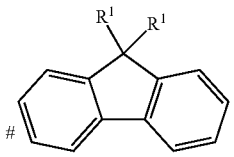     (Ar³-3)

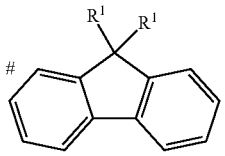     (Ar³-4)

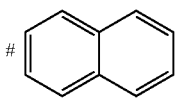     (Ar³-5)

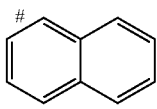     (Ar³-6)

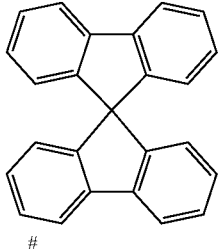     (Ar³-7)

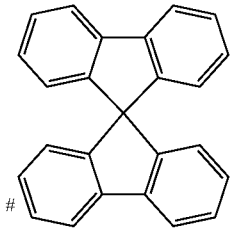     (Ar³-8)

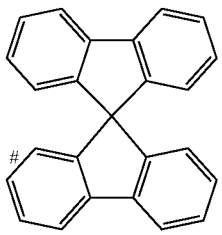     (Ar³-9)

-continued (Ar³-10)
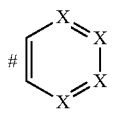

(Ar³-11)
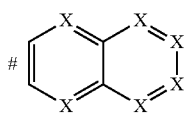

(Ar³-12)
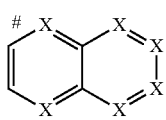

(Ar³-13)
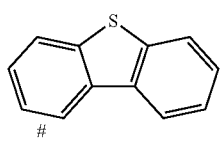

(Ar³-14)
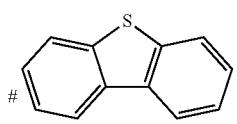

(Ar³-15)
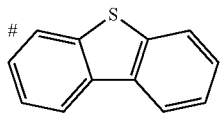

(Ar³-16)
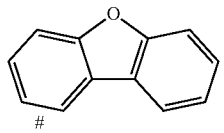

(Ar³-17)
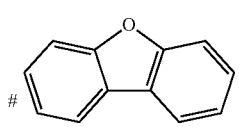

(Ar³-18)
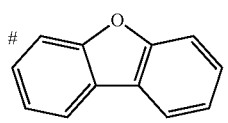

wherein
the bond denoted with # is the bond via which the Ar¹ group is fused to the adjacent Ar² group,
the groups are optionally substituted by radicals R³ at the positions shown as unsubstituted, and
X is the same or different in each instance and is N or CR³.

8. The compound of claim 1, wherein the compound is a compound of formula (I-1):

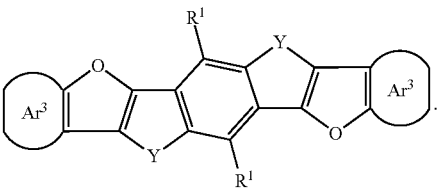

(I-1)

9. The compound of claim 1, wherein the value of the triplet level of the compound is greater than the value of the singlet level of the compound divided by 2.

10. A process for preparing the compound of claim 1, comprising the steps conducted in the following sequence:
i) reacting two compounds each containing a furan group and a compound containing the Ar¹ unit in an organometallic coupling reaction;
ii) reacting an ester group bonded to the Ar¹ unit and present in the compound to a tertiary alcohol group bonded to the same Ar¹ unit; and
iii) performing a ring-closure reaction of the tertiary alcohol group to form an alkylene bridge between the Ar¹ unit and the furan ring.

11. An oligomer, polymer, or dendrimer containing one or more compounds of claim 1, wherein the bond(s) to the polymer, oligomer, or dendrimer are optionally localized at any desired position substituted by R¹, R², or R³ in formula (I).

12. A formulation comprising at least one compound of claim 1 and at least one solvent.

13. A formulation comprising at least one oligomer, polymer or dendrimer of claim 11 and at least one solvent.

14. An electronic device selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes, and organic electroluminescent devices, wherein the electronic device comprises at least one compound of claim 1.

15. An electronic device selected from the group consisting of organic integrated circuits, organic field-effect transistors, organic thin-film transistors, organic light-emitting transistors, organic solar cells, organic optical detectors, organic photoreceptors, organic field-quench devices, organic light-emitting electrochemical cells, organic laser diodes, and organic electroluminescent devices, wherein the electronic device comprises at least one oligomer, polymer, or dendrimer of claim 11.

16. The electronic device of claim 13, wherein the electronic device is selected from the group consisting of organic electroluminescent devices comprising an anode, a cathode, an emitting layer, and optionally further organic layers, wherein the at least one compound is present as a matrix compound in combination with one or more emitting compounds in the emitting layer, or is present as emitting compound in combination with one or more matrix compounds in the emitting layer, or is present as hole-transporting compound in a layer arranged between anode and emitting layer.

17. The electronic device of claim 14, wherein the electronic device is selected from the group consisting of organic electroluminescent devices comprising an anode, a cathode, an emitting layer, and optionally further organic layers, wherein the at least one oligomer, polymer, or dendrimer is present as a matrix compound in combination with one or more emitting compounds in the emitting layer, or is present as emitting compound in combination with one or more matrix compounds in the emitting layer, or is present as hole-transporting compound in a layer arranged between anode and emitting layer.

\* \* \* \* \*